(12) United States Patent
Hassanzadeh Ghassabeh et al.

(10) Patent No.: US 12,668,622 B2
(45) Date of Patent: Jun. 30, 2026

(54) CALRETICULIN NANOBODIES

(71) Applicant: ACTINIUM PHARMACEUTICALS, INC., New York, NY (US)

(72) Inventors: Gholamreza Hassanzadeh Ghassabeh, Sint-Genesius-Rode (BE); Steve Schoonooghe, Holsbeek (BE); Helen Kotanides, Norwalk, CT (US)

(73) Assignee: ACTINIUM PHARMACEUTICALS, INC., New York, NY (US)

( * ) Notice: Subject to any disclaimer, the term of this patent is extended or adjusted under 35 U.S.C. 154(b) by 477 days.

(21) Appl. No.: 18/323,276

(22) Filed: May 24, 2023

(65) Prior Publication Data

US 2023/0416348 A1     Dec. 28, 2023

Related U.S. Application Data

(60) Provisional application No. 63/323,474, filed on Mar. 24, 2022.

(51) Int. Cl.
*C07K 16/18*          (2006.01)
*A61K 51/10*          (2006.01)

(52) U.S. Cl.
CPC .......... *C07K 16/18* (2013.01); *A61K 51/1018* (2013.01); *A61K 51/1096* (2013.01); *C07K 2317/22* (2013.01); *C07K 2317/569* (2013.01); *C07K 2317/92* (2013.01)

(58) Field of Classification Search
CPC ................ C07K 16/18; C07K 2317/22; C07K 2317/569; C07K 2317/92; A61K 51/1018; A61K 51/1096; A61K 51/1093
See application file for complete search history.

(56) References Cited

U.S. PATENT DOCUMENTS 9,603,954 B2      3/2017    Simon
10,420,851 B2     9/2019    Dave

FOREIGN PATENT DOCUMENTS

| AU | 2014259481 A1 | * | 11/2014 | |
| CN | 111289749 A | * | 6/2020 | ....... G01N 33/57438 |
| WO | 2017/155937 A1 | | 9/2017 | |
| WO | WO-2021095031 A2 | * | 5/2021 | ............. C07K 16/18 |

OTHER PUBLICATIONS

De Greve H, Virdi V, Bakshi S, Depicker A. Simplified monomeric VHH-Fc antibodies provide new opportunities for passive immunization. Curr Opin Biotechnol. 2020;61:96-101. (Year: 2020).*
Rashidian M, Ploegh H. Nanobodies as non-invasive imaging tools. Immunooncol Technol. 2020;7:2-14. (Year: 2020).*
Sugiura G, Kuhn H, Sauter M, Haberkorn U, Mier W. Radiolabeling strategies for tumor-targeting proteinaceous drugs. Molecules. 2014;19(2):2135-2165. (Year: 2014).*
Rowe, Raymond C, Paul J Sheskey, and Marian E Quinn. Handbook of Pharmaceutical Excipients. 6th ed. London: Pharmaceutical Press, 2009. Print. (Year: 2009).*

* cited by examiner

*Primary Examiner* — Joanne Hama
*Assistant Examiner* — Hannah Sunshine
(74) *Attorney, Agent, or Firm* — Michael E. Dukes; Dentons, Cohen & Grigsby, P.C.

(57) ABSTRACT

Provided are nanobodies that bind human calreticulin, fusion proteins including the nanobodies, pharmaceutical compositions including the nanobodies or fusion proteins, and radioconjugates of the nanobodies or fusion proteins.

21 Claims, 7 Drawing Sheets

Specification includes a Sequence Listing.

nbCRT clones, Binding Flow Cytometry

| Nb Clone | Nb SEQ ID NO: | CDR3 Group | CDR1 | CDR1 SEQ ID NO: | CDR2 | CDR2 SEQ ID NO: | CDR3 | CDR3 SEQ ID NO: |
|---|---|---|---|---|---|---|---|---|
| 2SPC3 | 72 | 1 | GITFRNSW | 1 | ISDGGGTT | 30 | STDMHGTG | 53 |
| 2SPC16 | 73 | 1 | GSIMSSYQ | 2 | ISEAGYTQ | 31 | ATDMTGTG | 54 |
| 2SPC17 | 74 | 1 | GITFRNSW | 1 | ISESGGTT | 32 | STDMHGTG | 53 |
| 2SPC28 | 75 | 1 | GITFRSSW | 3 | INESGGTT | 33 | STDMHGTG | 53 |
| 2SPC36 | 76 | 1 | GITFRNSW | 1 | ISESGGTT | 32 | STDMHGTG | 53 |
| 2SPC70 | 77 | 1 | DITFRNSW | 4 | ISESGGTT | 32 | STDTHGTG | 55 |
| 2SPC76 | 78 | 1 | GITFRNSW | 1 | ISESGGTT | 32 | STDMHGTG | 53 |
| 3SPC35 | 79 | 1 | GITFRSTW | 5 | INESGGTT | 33 | STDMHGTG | 53 |
| 3SPC44 | 80 | 1 | GTTFSNYW | 6 | ISESGGTT | 32 | STDMHGTG | 53 |
| 2SPC100 | 81 | 1 | DITFRNSW | 4 | ISESGGTT | 32 | STDMHGTG | 53 |
| 2SPC101 | 82 | 1 | GITFRSSW | 3 | INESGGTT | 33 | STDMHGTG | 53 |
| 2SPC104 | 83 | 1 | GFTFSNYR | 7 | ISEAGYTQ | 31 | ATDMTGTG | 54 |
| 2SPC117 | 84 | 1 | DITFRNSW | 4 | ISESGGTT | 32 | STDMHGTG | 53 |
| 2SPC118 | 85 | 1 | GITFRSTW | 5 | INESGGTT | 33 | STDMHGTG | 53 |
| 2SPC127 | 86 | 1 | GVTFRSSW | 8 | INESGGTT | 33 | STDMHGTD | 56 |
| 2SPC131 | 87 | 1 | GINFRNSW | 9 | ISDGGGTT | 30 | STDMHGTG | 53 |
| 2SPC136 | 88 | 1 | GINFRNSW | 9 | ISDGGGTT | 30 | STDMHGTG | 53 |
| 2SPC142 | 89 | 1 | GITFRSSW | 3 | INESGGTA | 34 | STDMHGTG | 53 |
| 2SPC148 | 90 | 1 | DITFRNSW | 4 | INESGGTT | 33 | STDMHGTG | 53 |
| 2SPC169 | 91 | 1 | GITFRSSW | 3 | INESGGTT | 33 | STDMHGTG | 53 |
| 3SPC106 | 92 | 1 | GITFRSSW | 3 | INESGGTT | 33 | STDMHGTG | 53 |
| 3SPC139 | 93 | 1 | GVTFRSSW | 8 | INESGGTT | 33 | STDMHGTG | 53 |
| 3SPC142 | 94 | 1 | GFMFSRHW | 10 | INESGGTT | 33 | STDMHGTG | 53 |
| 2TIC1 | 95 | 2 | NFLSSRFE | 11 | IFRDGNT | 35 | HVHILGRDY | 57 |

FIG. 1A

| Nb Clone | Nb SEQ ID NO: | CDR3 Group | CDR1 | CDR1 SEQ ID NO: | CDR2 | CDR2 SEQ ID NO: | CDR3 | CDR3 SEQ ID NO: |
|---|---|---|---|---|---|---|---|---|
| 2TIC18 | 96 | 2 | NFLSSRFE | 11 | IFRDGNT | 35 | HVHILGRDY | 57 |
| 3TIC33 | 97 | 2 | NFLSSRFE | 11 | IFRDGNT | 35 | HVHILGRDY | 57 |
| 3TIC47 | 98 | 2 | NFLSSRFE | 11 | IFRDGNT | 35 | HVHILGRDY | 57 |
| 3TIC74 | 99 | 2 | NFLSSRFE | 11 | IFRDGNT | 35 | HVHILGRDY | 57 |
| 3TIC90 | 100 | 2 | NFLSSRFE | 11 | IFRDGNT | 35 | HVHILGRDY | 57 |
| 3TIC91 | 101 | 2 | NFLSSRFE | 11 | IFRDENT | 36 | HVHILGRDY | 57 |
| 2TIC108 | 102 | 2 | NFLSSRFE | 11 | IFRDGNT | 35 | HVHILGRDY | 57 |
| 2TIC113 | 103 | 2 | NLLSSRFE | 12 | IFRDGNT | 35 | HVHILGRDY | 57 |
| 2TIC122 | 104 | 2 | NFLSSRFE | 11 | IFRDGMT | 37 | HVHILGRDY | 57 |
| 2TIC131 | 105 | 2 | NFLSSRFE | 11 | IFRDGNT | 35 | HVHILGRDY | 57 |
| 2TIC137 | 106 | 2 | NFLSSRFE | 11 | IFRDGNT | 35 | HVHILGRDY | 57 |
| 2TIC165 | 107 | 2 | NFLSSRFE | 11 | IFRDGNT | 35 | HVHILGRDY | 57 |
| 2TIC169 | 108 | 2 | NFLSSRFE | 11 | IFRDGNT | 35 | HVHILGRDY | 57 |
| 2TIC185 | 109 | 2 | NFLSSRFE | 11 | IFRDGNT | 35 | HVHILGRDY | 57 |
| 3TIC103 | 110 | 2 | NFLSSRFE | 11 | IFRDGNT | 35 | HVHILGRDY | 57 |
| 3TIC157 | 111 | 2 | NFLSSRFE | 11 | IFRDGNT | 35 | HVHILGRDY | 57 |
| 3TIC180 | 112 | 2 | NFLNSRFE | 13 | IFRDGTT | 38 | HVHILGRDY | 57 |
| 2SPC10 | 113 | 3 | GFVFSNYA | 14 | ITNSGSTT | 39 | GAVEPGAGLGASRDLLY | 58 |
| 3SPC54 | 114 | 3 | GFTFSAYA | 15 | ITNSGSTT | 39 | GAVEPGAGLGASRDLLY | 58 |
| 2SPC186 | 115 | 3 | GFVFSNYA | 14 | ITNSGSTT | 39 | GAVEPGAGLGASRDLLY | 58 |
| 3SPC145 | 116 | 3 | GFAFSDYH | 16 | ITNTGTTT | 40 | AAVKPGHGLGASRELLY | 59 |
| 3SPC159 | 117 | 3 | GSTLDYYA | 17 | ITNTGTTT | 40 | AAVKPGHGLGASRELLY | 59 |
| 3SPC186 | 118 | 3 | GFVFSNYA | 14 | ITNSGSTT | 39 | GAVEPGAGLGASRDLLY | 58 |
| 2SPC19 | 119 | 4 | GSIAA | 18 | MYVGGSI | 41 | NALVRFEGRNDDY | 60 |

FIG. 1B

| Nb Clone | Nb SEQ ID NO: | CDR3 Group | CDR1 | CDR1 SEQ ID NO: | CDR2 | CDR2 SEQ ID NO: | CDR3 | CDR3 SEQ ID NO: |
|---|---|---|---|---|---|---|---|---|
| 3SPC11 | 120 | 4 | GSIAA | 18 | MYVGGSI | 41 | NALVRFEGRNDDY | 60 |
| 2SPC154 | 121 | 4 | GSIAA | 18 | MYVGGSI | 41 | NALVRFEGRNDDY | 60 |
| 3SPC37 | 122 | 5 | GRMNTRTA | 19 | IDWTGDST | 42 | SDTSYGALRVHTAPSEYEH | 61 |
| 3SPC45 | 123 | 5 | GRMNTRTA | 19 | IDWTGDST | 42 | SDTSYGALRVHAAPSEYEH | 61 |
| 2TIC69 | 124 | 6 | NVMFSRFT | 20 | IARDGMT | 43 | NCQILGRDY | 62 |
| 3TIC109 | 125 | 6 | NVMFSRFT | 20 | IARDGMT | 43 | NCQILGRDY | 62 |
| 2TIC105 | 126 | 7 | TFPFTMNN | 21 | ITNDGSI | 44 | NRGTGPSYP | 63 |
| 2SPC50 | 127 | 8 | SSAFSLTP | 22 | ITTGSTV | 45 | NRIYIGDTFPPWN | 64 |
| 3SPC26 | 128 | 9 | GFTFSSYQ | 23 | ISTNGGII | 46 | ARCDVAYWSDSCD | 65 |
| 3SPC27 | 129 | 10 | GSILRINT | 24 | ITSGGRP | 47 | NVYARLTGSDSYLAY | 66 |
| 3SPC57 | 130 | 11 | GGAFTTYS | 25 | INKSGKT | 48 | AASVADGVFVGTNMYHY | 67 |
| 3TIC34 | 131 | 12 | GGTFSNYG | 26 | INWSGAIT | 49 | AAVTRYGGYADSRPQWYDS | 68 |
| 2SPC81 | 132 | 13 | GRTFSYSAMGGDV | 27 | ISGSGAST | 50 | AAAPRTYYGTNYRNKGEYDY | 69 |
| 2SPC31 | 133 | 14 | GGTLSSYA | 28 | ISRTDGRT | 51 | AAGMGVSAYSSGGYFNAERYDY | 70 |
| 2SPC135 | 134 | 15 | GRTSSRYA | 29 | VSFSGDST | 52 | ASRPPGPAYSDTAYSRAYEYNY | 71 |

FIG. 1C

| hCRT Nb Clone | SEQ ID NO: | CDR3 Group | ELISA hCRT Binding Data | | Dissociation Rate | |
|---|---|---|---|---|---|---|
| | | | ELISA hCRT Nb | ELISA Control | hCRT/ Control | koff | koff SE |

| hCRT Nb Clone | SEQ ID NO: | CDR3 Group | ELISA hCRT Nb | ELISA Control | hCRT/ Control | koff | koff SE |
|---|---|---|---|---|---|---|---|
| 2SPC3 | 72 | 1 | 1.5307 | 0.1392 | 10.99640805 | 4.36E-03 | 8.79E-05 |
| 2SPC16 | 73 | 1 | 1.4346 | 0.1305 | 10.99310345 | 2.50E-03 | 6.84E-05 |
| 2SPC17 | 74 | 1 | 0.5748 | 0.1066 | 5.392120075 | 3.44E-03 | 9.73E-05 |
| 2SPC28 | 75 | 1 | 1.6095 | 0.1193 | 13.49119866 | 2.38E-03 | 8.84E-05 |
| 2SPC36 | 76 | 1 | 1.6296 | 0.1711 | 9.524254822 | 3.75E-03 | 7.51E-05 |
| 2SPC70 | 77 | 1 | 0.6247 | 0.1371 | 4.556528082 | 3.82E-03 | 8.80E-05 |
| 2SPC76 | 78 | 1 | 1.3243 | 0.1455 | 9.101718213 | 4.44E-03 | 8.88E-05 |
| 2SPC100 | 81 | 1 | 0.6013 | 0.1107 | 5.431797651 | 3.79E-03 | 8.12E-05 |
| 2SPC101 | 82 | 1 | 0.4627 | 0.1048 | 4.415076336 | 3.34E-03 | 7.01E-05 |
| 2SPC104 | 83 | 1 | 1.0852 | 0.1606 | 6.757160648 | 3.98E-03 | 6.26E-05 |
| 2SPC117 | 84 | 1 | 0.5103 | 0.1132 | 4.50795053 | 4.00E-03 | 7.30E-05 |
| 2SPC118 | 85 | 1 | 0.7665 | 0.1193 | 6.424979044 | 3.65E-03 | 7.91E-05 |
| 2SPC127 | 86 | 1 | 0.6862 | 0.1338 | 5.128550075 | 3.66E-03 | 6.93E-05 |
| 2SPC131 | 87 | 1 | 0.7123 | 0.1464 | 4.865437158 | 3.17E-03 | 6.40E-05 |
| 2SPC136 | 88 | 1 | 0.5719 | 0.1738 | 3.290563867 | 2.83E-03 | 5.71E-05 |
| 2SPC142 | 89 | 1 | 0.509 | 0.168 | 3.029761905 | 3.33E-03 | 6.49E-05 |
| 2SPC148 | 90 | 1 | 0.986 | 0.1263 | 7.806809184 | 3.97E-03 | 7.93E-05 |
| 2SPC169 | 91 | 1 | 0.9367 | 0.1228 | 7.627850163 | 2.80E-03 | 6.51E-05 |
| 3SPC35 | 79 | 1 | 1.5869 | 0.1182 | 13.42554992 | NA | NA |
| 3SPC44 | 80 | 1 | 0.4233 | 0.1127 | 3.755989352 | 3.41E-03 | 8.20E-05 |
| 3SPC106 | 92 | 1 | 0.9882 | 0.1067 | 9.261480787 | NA | NA |
| 3SPC139 | 93 | 1 | 0.7385 | 0.1389 | 5.316774658 | 1.84E-03 | 7.87E-05 |
| 3SPC142 | 94 | 1 | 0.523 | 0.1568 | 3.335459184 | 2.02E-03 | 4.93E-05 |

FIG. 2A

| hCRT Nb Clone | SEQ ID NO: | CDR3 Group | ELISA hCRT Binding Data | | | Dissociation Rate | |
|---|---|---|---|---|---|---|---|
| | | | ELISA hCRT Nb | ELISA Control | hCRT/ Control | koff | koff SE |
| 2TIC1 | 95 | 2 | 1.3204 | 0.1404 | 9.404558405 | 1.84E-03 | 4.77E-05 |
| 2TIC18 | 96 | 2 | 1.3289 | 0.1172 | 11.3387372 | 3.19E-03 | 8.91E-05 |
| 2TIC108 | 102 | 2 | 1.1152 | 0.0934 | 11.94004283 | 2.60E-03 | 5.93E-05 |
| 2TIC113 | 103 | 2 | 0.401 | 0.0823 | 4.872417983 | 2.52E-03 | 5.22E-05 |
| 2TIC122 | 104 | 2 | 1.4463 | 0.0912 | 15.85855263 | 2.34E-03 | 6.18E-05 |
| 2TIC131 | 105 | 2 | 0.9326 | 0.1002 | 9.30738523 | 2.61E-03 | 6.57E-05 |
| 2TIC137 | 106 | 2 | 0.8824 | 0.0915 | 9.643715847 | 2.97E-03 | 9.75E-05 |
| 2TIC165 | 107 | 2 | 1.2934 | 0.0844 | 15.32464455 | 3.25E-03 | 5.76E-05 |
| 2TIC169 | 108 | 2 | 1.2173 | 0.0857 | 14.2042007 | 4.08E-03 | 7.96E-05 |
| 2TIC185 | 109 | 2 | 0.8264 | 0.0934 | 8.847965739 | 2.61E-03 | 6.12E-05 |
| 3TIC33 | 97 | 2 | 1.1457 | 0.1336 | 8.575598802 | 2.86E-03 | 6.47E-05 |
| 3TIC47 | 98 | 2 | 0.8401 | 0.1289 | 6.517455392 | 2.78E-03 | 4.56E-05 |
| 3TIC74 | 99 | 2 | 1.1401 | 0.1345 | 8.476579926 | NA | NA |
| 3TIC90 | 100 | 2 | 0.5804 | 0.0924 | 6.281385281 | 2.99E-03 | 6.36E-05 |
| 3TIC91 | 101 | 2 | 1.1587 | 0.2116 | 5.475897921 | 2.58E-03 | 6.97E-05 |
| 3TIC103 | 110 | 2 | 1.0894 | 0.0821 | 13.26918392 | 2.26E-03 | 6.84E-05 |
| 3TIC157 | 111 | 2 | 1.1261 | 0.0889 | 12.66704162 | 1.78E-03 | 3.95E-05 |
| 3TIC180 | 112 | 2 | 0.9063 | 0.1201 | 7.54621149 | 1.75E-03 | 5.74E-05 |
| 2SPC10 | 113 | 3 | 3.7865 | 0.3087 | 12.265954 | NA | NA |
| 2SPC186 | 115 | 3 | 1.8925 | 0.1395 | 13.56630824 | 2.10E-03 | 6.81E-05 |
| 3SPC54 | 114 | 3 | 1.4517 | 0.0984 | 14.75304878 | 1.98E-03 | 5.00E-05 |
| 3SPC145 | 116 | 3 | 0.4305 | 0.1161 | 3.708010336 | 2.36E-03 | 5.78E-05 |
| 3SPC159 | 117 | 3 | 0.5825 | 0.1275 | 4.568627451 | 2.10E-03 | 4.62E-05 |

FIG. 2B

| hCRT Nb Clone | SEQ ID NO: | CDR3 Group | ELISA hCRT Binding Data | | | Dissociation Rate | |
| | | | ELISA hCRT Nb | ELISA Control | hCRT/ Control | koff | koff SE |
|---|---|---|---|---|---|---|---|
| 3SPC186 | 118 | 3 | 1.7045 | 0.1337 | 12.7486911 | 1.80E-03 | 4.74E-05 |
| 2SPC19 | 119 | 4 | 3.215 | 0.1216 | 26.43914474 | 2.34E-03 | 8.24E-05 |
| 2SPC154 | 121 | 4 | 0.8543 | 0.1384 | 6.172687861 | 3.42E-03 | 6.99E-05 |
| 3SPC11 | 120 | 4 | 3.0255 | 0.113 | 26.77433628 | 2.08E-03 | 5.46E-05 |
| 3SPC37 | 122 | 5 | 0.6024 | 0.1752 | 3.438356164 | NA | NA |
| 3SPC45 | 123 | 5 | 0.6196 | 0.1271 | 4.874901652 | 2.14E-03 | 7.06E-05 |
| 2TIC69 | 124 | 6 | 0.8297 | 0.1936 | 4.285640496 | 2.19E-03 | 5.97E-05 |
| 3TIC109 | 125 | 6 | 0.7915 | 0.085 | 9.311764706 | 1.90E-03 | 5.89E-05 |
| 2TIC105 | 126 | 7 | 0.5303 | 0.0806 | 6.579404467 | 1.89E-03 | 8.32E-05 |
| 2SPC50 | 127 | 8 | 0.6045 | 0.1897 | 3.186610438 | 3.52E-03 | 8.06E-05 |
| 3SPC26 | 128 | 9 | 0.5572 | 0.0921 | 6.049945711 | 2.58E-03 | 5.76E-05 |
| 3SPC27 | 129 | 10 | 0.7567 | 0.1856 | 4.077047414 | NA | NA |
| 3SPC57 | 130 | 11 | 1.4281 | 0.1293 | 11.04485692 | 1.87E-03 | 5.27E-05 |
| 3TIC34 | 131 | 12 | 3.8012 | 0.1098 | 34.61930783 | 2.95E-02 | 8.83E-04 |
| 2SPC81 | 132 | 13 | 0.5184 | 0.1577 | 3.28725428 | 3.76E-03 | 7.78E-05 |
| 2SPC31 | 133 | 14 | 0.5454 | 0.1764 | 3.091836735 | 1.76E-03 | 7.88E-05 |
| 2SPC135 | 134 | 15 | 0.4615 | 0.137 | 3.368613139 | 2.55E-03 | 7.12E-05 |

NA – not available

Negative control Nb – BCII10

FIG. 2C

CALRETICULIN NANOBODIES

CROSS-REFERENCE TO RELATED APPLICATIONS

This application claims the benefit of U.S. provisional application Ser. No. 63/323,474 filed Mar. 24, 2022 which is hereby incorporated by reference in its entirety.

SEQUENCE LISTING

The instant application contains a Sequence Listing which has been submitted electronically in XML format and is hereby incorporated by reference in its entirety. Said XML copy, created on Aug. 28, 2023 is named ATNM-018US_ SL.xml and is 192,317 bytes in size.

FIELD OF THE INVENTION

The presently claimed invention relates to the field of nanobody-based therapeutics.

BACKGROUND

Calreticulin is a 46 kDa chaperone protein that predominantly resides in the endoplasmic reticulum (ER), facilitating protein folding and maintaining calcium homeostasis. Calreticulin is composed of three domains: (1) the globular N domain, which consists of eight antiparallel β-strands, contains polypeptide-, carbohydrate-, and zinc-binding sites; (2) the P domain, which binds to calcium with high affinity but low capacity, contains three antiparallel β-strands and is associated with lectin-like chaperone function; and (3) the C domain, which binds to calcium with low affinity but high capacity (owing to the highly acidic amino acid composition). Importantly, the C-terminal region contains the KDEL (Lys-Asp-Glu-Leu) ER retention signal. Along with various other chaperone proteins, calreticulin maintains quality control over newly synthesized proteins, preventing export of misfolded, dysfunctional protein from the ER.

Although lacking a transmembrane domain, calreticulin can also be presented on the cell surface. Cellular stressors promote the relocalization of calreticulin from the ER to the outer leaflet of the plasma membrane, where it can serve as an immune-stimulating danger associated molecular pattern (DAMP). Calreticulin is also presented on the surface of various human cancer cells in vivo, while such cell surface expression of calreticulin is atypical for normal cells in the absence of stress or damage. Cell surface calreticulin may be recognized by LRP1 expressed on phagocytic cells, which engulf and clear the calreticulin-exposed stressed cells. However, various cancers employ mechanisms to evade such phagocytosis.

What is needed and provided by the various aspects of the present invention are new targeting agents against cell surface Calreticulin.

SUMMARY OF THE INVENTION

One aspect of the invention provides an anti-(human Calreticulin) nanobody or a fusion protein including an anti-(human calreticulin) nanobody amino acid sequence, the nanobody or fusion protein including:
   (i) a nanobody amino acid sequence including the CDRs (CDR1, CDR2 and CDR3) of any of the nanobodies disclosed herein, i.e., of any of the nanobodies set forth in SEQ ID NOS:72-134;

(ii) a nanobody amino acid sequence including the framework regions and the CDRs of any of the nanobodies disclosed herein, i.e., of any of the nanobodies set forth in SEQ ID NOS:72-134; or
   (iii) a nanobody amino acid sequence including the full nanobody amino acid sequence of any of the nanobody sequences disclosed herein, i.e., any of the nanobody sequences set forth in SEQ ID NOS:72-134.

Additional features, advantages, and aspects of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 1A identifies the full amino acid sequence, the CDR3 group, and the CDR amino acid sequences for each of twenty-four (24) human calreticulin binding nanobody clones.

FIG. 1B identifies the full amino acid sequence, the CDR3 group, and the CDR amino acid sequences for each of twenty-four (24) human calreticulin binding nanobody clones.

FIG. 1C identifies the full amino acid sequence, the CDR3 group, and the CDR amino acid sequences for each of fifteen (15) human calreticulin binding nanobody clones.

FIG. 2A sets forth the clone name, VHH sequence, CDR3 group, ELISA hCRT binding data, and bio-layer interferometry (BLI) hCRT off-rate data for twenty-three (23) of the anti-hCRT nanobody clones.

FIG. 2B sets forth the clone name, VHH sequence, CDR3 group, ELISA hCRT binding data, and bio-layer interferometry (BLI) hCRT off-rate data for twenty-three (23) of the anti-hCRT nanobody clones.

FIG. 2C sets forth the clone name, VHH sequence, CDR3 group, ELISA hCRT binding data, and bio-layer interferometry (BLI) hCRT off-rate data for seventeen (17) of the anti-hCRT nanobody clones.

DETAILED DESCRIPTION

Figure 3:
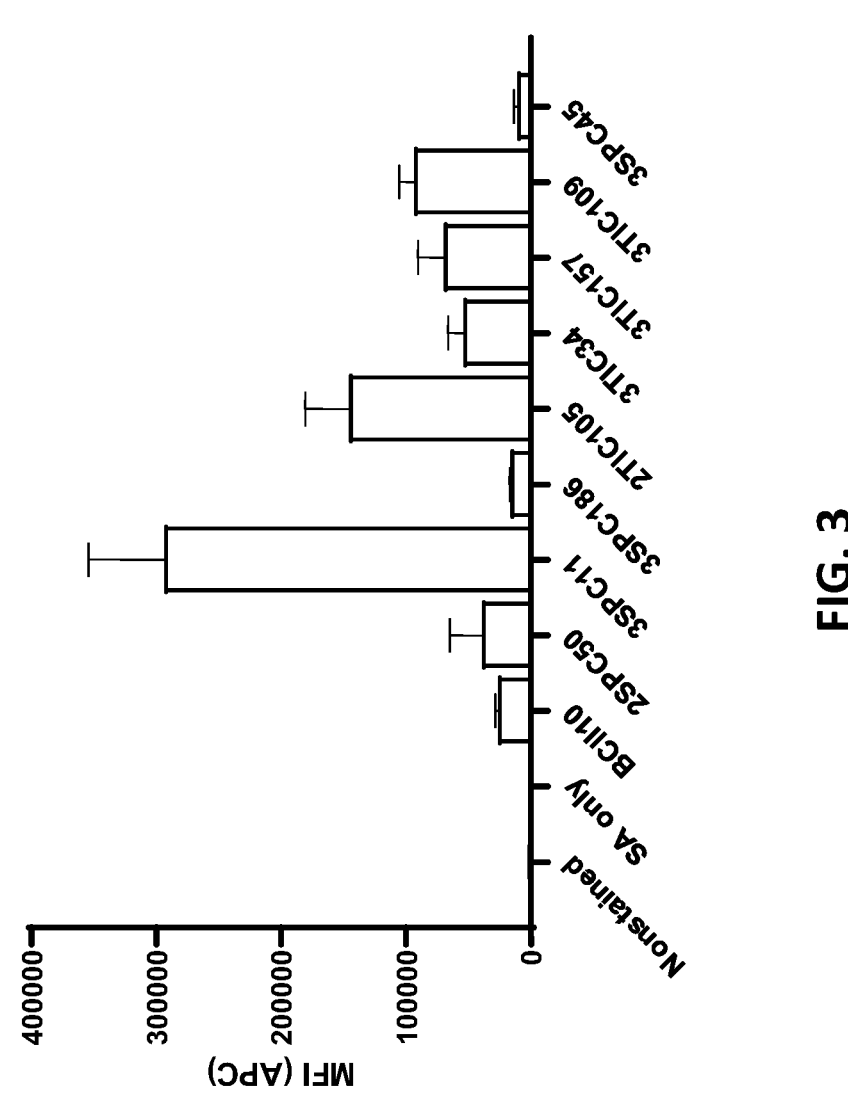
FIG. 3 shows the flow cytometric cell binding data for eight (8) of the anti-hCRT nanobody clones, non-stained (cells only) control, secondary antibody only (no primary nanobody/antibody) control denoted "SA only" and non-specific primary nanobody BCII10 control.

A nanobody (Nb) or VHH domain antibody is the variable region of a camelid heavy chain-only antibody. The present invention provides nanobodies and nanobody fusion proteins that specifically bind human calreticulin (hCalreticulin, hCRT) and related compositions and methods of use thereof.

One aspect of the invention provides an anti-hCalreticulin nanobody or a fusion protein including an anti-hCalreticulin nanobody amino acid sequence, the nanobody or fusion protein including:
   (i) a nanobody amino acid sequence including the CDRs (CDR1, CDR2 and CDR3) of any of the nanobodies disclosed herein, i.e., of any of SEQ ID NOS:72-134;
   (ii) a nanobody amino acid sequence including the framework regions and the CDRs of any of the nanobodies disclosed herein i.e., of any of SEQ ID NOS:72-134; or (iii) a nanobody amino acid sequence including the full nanobody amino acid sequence of any of the nanobody sequences disclosed herein, i.e., of any of SEQ ID NOS:72-134.

FIG. 1A identifies the full amino acid sequence (SEQ ID NOS:72-95, respectively), the CDR3 group, and the CDR amino acid sequences for each of the human calreticulin binding nanobody clones designated 2SPC3, 2SPC16, 2SPC17, 2SPC28, 2SPC36, 2SPC70, 2SPC76, 3SPC35, 3SPC44, 2SPC100, 2SPC101, 2SPC104, 2SPC117, 2SPC118, 2SPC127, 2SPC131, 2SPC136, 2SPC142, 2SPC148, 2SPC169, 3SPC106, 3SPC139, 3SPC142, and 2TIC1.

FIG. 1B identifies the full amino acid sequence (SEQ ID NOS:96-119, respectively), the CDR3 group, and the CDR amino acid sequences for each of the human calreticulin binding nanobody clones designated 2TIC18, 3TIC33, 3TIC47, 3TIC74, 3TIC90, 3TIC91, 2TIC108, 2TIC113, 2TIC122, 2TIC131, 2TIC137, 2TIC165, 2TIC169, 2TIC185, 3TIC103, 3TIC157, 3TIC180, 2SPC10, 3SPC54, 2SPC186, 3SPC145, 3SPC159, 3SPC186, and 2SPC19.

FIG. 1C identifies the full amino acid sequence (SEQ ID NOS:120-134, respectively), the CDR3 group, and the CDR amino acid sequences for each of the human calreticulin binding nanobody clones designated 3SPC11, 2SPC154, 3SPC37, 3SPC45, 2TIC69, 3TIC109, 2TIC105, 2SPC50, 3SPC26, 3SPC27, 3SPC57, 3TIC34, 2SPC81, 2SPC31, and 2SPC135.

The CDR sequences of the nanobody clones are delineated according to the IMGT numbering convention. The CDRs are surrounded by VHH domain framework regions (FRs) in the following manner: FR1 is the amino acid sequence preceding (N-terminal to) CDR1, FR2 is the amino acid sequence between CDR1 and CDR2, FR3 is the amino acid sequence between CDR2 and CDR3, and FR4 is the amino acid sequence following (C-terminal to) CDR3 to the end of the nanobody (VHH domain) sequence.

FIG. 2A sets forth the clone name, VHH sequence, CDR3 group, ELISA hCRT binding data (control is not coated with hCRT), and bio-layer interferometry (BLI) hCRT off-rate data for twenty-three (23) of the anti-hCRT nanobody clones.

FIG. 2B sets forth the clone name, VHH sequence, CDR3 group, ELISA hCRT binding data (control is not coated with hCRT), and bio-layer interferometry (BLI) hCRT off-rate data for twenty-three (23) of the anti-hCRT nanobody clones.

FIG. 2C sets forth the clone name, VHH sequence, CDR3 group, ELISA hCRT binding data (control is not coated with hCRT), and bio-layer interferometry (BLI) hCRT off-rate data for seventeen (17) of the anti-hCRT nanobody clones.

The hCRT off rates for the 63 anti-hCRT nanobody clones (presented in FIGS. 2A-C) were determined by bio-layer interferometry (BLI) using an Octet Red® instrument (ForteBio, Fremont, California, USA) and Fortebio Data Analysis Software, using a 1:1 binding model. A total absence of binding signal was observed for the negative (non-hCRT-specific) control nanobody BCII10. The majority of the nanobodies tested showed reliable binding responses higher than 0.1 nm. Where data was available, with the exception of one clone, all the nanobodies showed a very strong k-off which was always below about $5\times10\text{-}3$ 1/s.

FIG. 3 shows the flow cytometric cell binding data for eight (8) of the anti-hCRT nanobody clones, non-stained (cells only) control, secondary antibody only (no primary nanobody/antibody) control denoted "SA only" and non-specific primary nanobody BCII10 control. In brief, in vitro cell binding properties of eight anti-hCRT nanobody clones were evaluated by incubating 400 ug/ml (100 uL) unmodified nanobodies with acute promyelocytic leukemia cells (HL-60 cell line; ATCC CCL-240) for 1 h at 4° C. A fluorescently labeled secondary antibody (Goat Anti-Alpaca-AF647 [Jackson ImmunoResearch Laboratories, Inc., West Grove, Pennsylvania, USA] (1:500 dilution)) was added and incubated for 1 h at 4° C. The samples were then analyzed using a flow cytometer and the data was analyzed using BD Accuri® C6 Plus Software. Clones 3SPC11 (SEQ ID NO:120), 2TIC105 (SEQ ID NO:126), 3TIC109 (SEQ ID NO:125), 3TIC157 (SEQ ID NO:111), and 3TIC34 (SEQ ID NO:131) specifically bound HL60 cells in the assay.

Another aspect of the invention provides a protein that includes one or more of the human Calreticulin binding nanobody amino acid sequences set forth in SEQ ID NOS: 72-134. Such a protein may, for example, consist of one nanobody amino acid sequence alone, include multiple nanobody sequences that are the same or different, or include the one or more of the nanobody sequences and an affinity tag, such as an epitope tag and/or metal-binding tag, or include an Fc constant region, such as a human Fc constant region.

A related aspect of the invention provides a protein, such as a nanobody or a fusion protein including a nanobody amino acid sequence, that includes a nanobody (VHH) amino acid sequence including the CDR combination (of CDR1, CDR2, and CDR3) found in any one of the anti-hCRT nanobody sequences set forth in SEQ ID NOS:72-134 as shown in FIGS. 1A-1C, and in Table 1 below (indicating exemplary human Calreticulin binding nanobody sequences and, to the right of each in the table, its respective CDR1, CDR2, and CDR3 amino acid sequences).

TABLE 1

| Nb Clone | Nb SEQ ID NO: | CDR1 SEQ ID NO: | CDR2 SEQ ID NO: | CDR3 SEQ ID NO: |
|---|---|---|---|---|
| 2SPC3 | 72 | 1 | 30 | 53 |
| 2SPC16 | 73 | 2 | 31 | 54 |
| 2SPC17 | 74 | 1 | 32 | 53 |
| 2SPC28 | 75 | 3 | 33 | 53 |
| 2SPC70 | 77 | 4 | 32 | 55 |
| 3SPC35 | 79 | 5 | 33 | 53 |
| 3SPC44 | 80 | 6 | 32 | 53 |
| 2SPC100 | 81 | 4 | 32 | 53 |
| 2SPC104 | 83 | 7 | 31 | 54 |
| 2SPC127 | 86 | 8 | 33 | 56 |
| 2SPC131 | 87 | 9 | 30 | 53 |
| 2SPC142 | 89 | 3 | 34 | 53 |
| 2SPC148 | 90 | 4 | 33 | 53 |
| 3SPC139 | 93 | 8 | 33 | 53 |
| 3SPC142 | 94 | 10 | 33 | 53 |
| 2TIC1 | 95 | 11 | 35 | 57 |
| 3TIC90 | 100 | 11 | 36 | 57 |
| 2TIC113 | 103 | 12 | 35 | 57 |
| 2TIC122 | 104 | 11 | 37 | 57 |
| 3TIC180 | 112 | 13 | 38 | 57 |
| 2SPC10 | 113 | 14 | 39 | 58 |
| 3SPC54 | 114 | 15 | 39 | 58 |
| 3SPC145 | 116 | 16 | 40 | 59 |
| 3SPC159 | 117 | 17 | 40 | 59 |
| 2SPC19 | 119 | 18 | 41 | 60 |
| 3SPC37 | 122 | 19 | 42 | 61 |
| 2TIC69 | 124 | 20 | 43 | 62 |
| 2TIC105 | 126 | 21 | 44 | 63 |
| 2SPC50 | 127 | 22 | 45 | 64 |
| 3SPC26 | 128 | 23 | 46 | 65 |
| 3SPC27 | 129 | 24 | 47 | 66 |
| 3SPC57 | 130 | 25 | 48 | 67 |

TABLE 1-continued

| Nb Clone | Nb SEQ ID NO: | CDR1 SEQ ID NO: | CDR2 SEQ ID NO: | CDR3 SEQ ID NO: |
|---|---|---|---|---|
| 3TIC34 | 131 | 26 | 49 | 68 |
| 2SPC81 | 132 | 27 | 50 | 69 |
| 2SPC31 | 133 | 28 | 51 | 70 |
| 2SPC135 | 134 | 29 | 52 | 71 |

Any of the nanobodies disclosed herein may further include an affinity tag such as an epitope tag and/or a metal-binding tag. For example, any of the nanobodies disclosed herein may further include an amino terminal combination hemagglutinin (HA) epitope and polyhistidine tag having the sequence AAAYPYDVPDYGSHHHHHH (SEQ ID NO: 135).

The invention also provides fusion proteins that include any of the CRT-binding nanobodies disclosed herein and an N-terminal, camelid or non-camelid immunoglobulin Fc region, such as the human IgG1 Fc region set forth in SEQ ID NO:136. The Fc sequence may, for example, begin immediately after the N-terminal SS of the nanobody (VHH) sequence in the fusion protein or may be preceded by a linker sequence which may, for example, be derived from an immunoglobulin hinge region. For example, the Fc portion may be connected to the nanobody (VHH) portion via a linker peptide disposed as the N-terminal end of the nanobody sequence, so that the amino-to-carboxyl arrangement of elements is nanobody—linker—Fc.

The linker peptide may, for example, include the sequence STMVRS (SEQ ID NO: 137), EPKSCDKTHTCPPCP (SEQ ID NO:139; derived from human IgG1 hinge region), or VPRDCGCKPCICT (SEQ ID NO:141; derived from mouse IgG1 hinge region).

The Fc region may, for example, include the sequence:

```
DKTHTCPPCPAPELLGGPSVFLFPPKPKDTLMISRTPEVTCVVVDVSHE

DPEVKFNWYVDGVEVHNAKTICPREEQYNSTYRVVSVLTVLHQDWLNGI

CEYKCKVSNICALPAPIEKTISICAKGQPREPOVYTLPPSREEMTICNO

VSLTCLVKGFYPSDIAVEWESNGQPENNYKTITTVLDSDGSFFLYSICL

TVDKSRWQQGNVFSCSVMHEALHNHYTQKSLSLSPGK
(SEQ ID NO: 138; human Fc gammal type with
N-terminal hinge region);

APELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCS

VMHEALHNHYTQKSLSLSPGK
(SEQ ID NO: 140; human Fc gammal type);
or

VPEVSSVFIFPPKPKDVLTITLTPKVTCVVVDISKDDPEVQFSWFVDDV

EVHTAQTQPREEQFNSTFRSVSELPIMHQDWLNGKEFKCRVNSAAFPAP

IEKTISKTKGRPKAPQVYTIPPPKEQMAKDKVSLTCMITDFFPEDITVE

WQWNGQPAENYKNTQPIMNTNGSYFVYSKLNVQKSNWEAGNTFTCSVLH

EGLHNHHTEKSLSHSPGK
(SEQ ID NO: 142; mouse Fc gammal type).
```

Suitable pairings of linker sequences and Fc region sequences that may be used in a nanobody Fc fusion protein include, for example, SEQ ID NO:137 with SEQ ID NO:138, SEQ ID NO:139 with SEQ ID NO:140, and SEQ ID NO:141 with SEQ ID NO:142.

Cell surface expression of Calreticulin is upregulated in cells undergoing stress and in malignant cells. The nanobodies or nanobody fusion proteins disclosed herein may, for example, be linked directly or indirectly via a chemically conjugated chelator, to a radionuclide, for example, to target cytotoxic radiation to Calreticulin-expressing cells in mammalian subject such as a human patient, and/or to non-cytotoxically image Calreticulin-expression in a mammalian subject such as a human patient. For example, the nanobody or nanobody fusion protein may be directly labeled with $^{131}$I according to the methods disclosed in U.S. Pat. No. 10,420,851 or the nanobody or nanobody fusion protein may be chemically conjugated to a chelator, such as p-SCN-DOTA and labeled with a radionuclide such as $^{225}$Ac, according to the procedures described in U.S. Pat. No. 9,603,954. More generally, for radiolabeling, suitable radionuclides include but are not limited to $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{131}$I, $^{125}$I, $^{82}$Rb, $^{86}$Y, $^{87}$Y, $^{90}$Y, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb $^{212}$Pb, $^{212}$Bi, $^{213}$Bi, $^{225}$Ac, and $^{227}$Th.

The chelator group in the various aspects of the invention may, for example, include: 1,4,7,10-tetraazacyclododecane-1,4,7-triacetic acid (DO3A) or a derivative thereof, 1,4,7-triazacyclononane-1,4-diacetic acid (NODA) or a derivative thereof, 1,4,7-triazacyclononane-1,4,7-triacetic acid (NOTA) or a derivative thereof; 1,4,7,10-tetraazacyclodo-decane-1,4,7,10-tetraacetic acid (DOTA) or a derivative thereof, 1,4,7-triazacyclononane, 1-glutaric acid-4,7-di-acetic acid (NODAGA) or a derivative thereof; 1,4,7,10-tetraazacyclodecane, 1-glutaric acid-4,7,10-triacetic acid (DOTAGA) or a derivative thereof; 1,4,8,11-tetraazacyclo-tetradecane-1,4,8,11-tetraacetic acid (TETA) or a derivative thereof, 1,4,8,11-tetraazabicyclo[6.6.2]hexadecane-4,11-di-acetic acid (CB-TE2A) or a derivative thereof; diethylene triamine pentaacetic acid (DTPA), its diester, or a derivative thereof; 2-cyclohexyl diethylene triamine pentaacetic acid (CHX-A"-DTPA) or a derivative thereof, deforoxamine (DFO) or a derivative thereof, 1,2-[[6-carboxypyridin-2-yl] methylamino]ethane (H₂dedpa) or a derivative thereof, DADA or a derivative thereof; 1,4,7,10-Tetraazacyclodode-cane-1,4,7,10-tetra(methylene phosphonic acid) (DOTP) or a derivative thereof; 4-amino-6-[[16-[(6-carboxypyridin-2-yl)methyl]-1,4,10,13-tetraoxa-7,16-diazacyclooctadec-7-yl] methyl]pyridine-2-carboxylic acid (MACROPA-NH₂) or a derivative thereof, MACROPA or a derivative thereof, 1,4, 7,10-tetrakis(carbamoylmethyl)-1,4,7,10-tetraazacyclodo-decane (TCMC) or a derivative thereof; {4-[2-(bis-car-boxymethylamino)-ethyl]-7-carboxymethyl-[1,4,7] triazonan-1-yl}-acetic acid (NETA) or a derivative thereof, Diamsar or a derivative thereof; 1,4,7-triazacyclononane-1, 4,7-tris[methyl(2-carboxyethyl)phosphinic acid (TRAP, PRP9, TRAP-Pr) or a derivative thereof; N,N'-bis(6-car-boxy-2-pyridylmethyl)ethylenediamine-N,N'-diacetic acid (H4octapa) or a derivative thereof; N,N'-[1-benzyl-1,2,3-triazole-4-yl]methyl-N,N'-[6-(carboxy)pyridin-2-yl]-1,2-di-aminoethane (H2azapa) or a derivative thereof; N,N"-[[6-(carboxy)pyridin-2-yl]methyl]diethylenetriamine-N,N',N"-triacetic acid (H5decapa) or a derivative thereof, N,N'-bis (2-hydroxy-5-sulfobenzyl)ethylenediamine-N,N'-diacetic acid (SHBED) or a derivative thereof; N,N'-bis(2-hydroxy-benzyl)ethylenediamine-N,N'-diacetic acid (HBED) or a derivative thereof; 3,6,9,15-tetraazabicyclo[9.3.1]penta-deca-1(15),11,13-triene-3,6,9,-triacetic acid (PCTA) or a derivative thereof; desferrioxamine B (DFO) or a derivative thereof; N,N'-(methylenephosphonate)-N,N'-[6-(methoxy-carbonyl)pyridin-2-yl]methyl-1,2-diaminoethane (H6phospa) or a derivative thereof; 1,4,7,10,13,16-hexaaza-cyclohexadecane-N,N',N'',N''',N'''',N''''''-hexaacetic acid (HEHA) or a derivative thereof, 1,4,7,10,13-pentaazacyclo-pentadecane-N,N',N'',N''',N''''-pentaacetic acid (PEPA) or a derivative thereof, or 3,4,3-LI(1,2-HOPO) or a derivative thereof.

The nanobodies or nanobody fusion proteins may, for example, also be linked to one or more cytotoxic drugs to target and deplete Calreticulin-expressing cells in a mammalian subject such as a human patient. Thus, one aspect of the invention provides an antibody-drug-conjugate (ADC) that includes a nanobody amino acid sequence as disclosed herein as a component.

The words "comprising" and forms of the word "comprising" as well as the word "including" and forms of the word "including," as used in this description and in the claims, do not limit the inclusion of elements beyond what is referred to. Additionally, although throughout the present disclosure various aspects or elements thereof are described in terms of "including" or "comprising," corresponding aspects or elements thereof described in terms of "consisting essentially of" or "consisting of" are similarly disclosed. For example, while certain aspects of the invention have been described in terms of a method "including" or "comprising" administering a radiolabeled targeting agent, corresponding methods instead reciting "consisting essentially of" or "consisting of" administering the radiolabeled target are also within the scope of said aspects and disclosed by this disclosure.

In addition, compositions including a radiolabeled anti-Calreticulin nanobody or nanobody fusion protein may include one or more pharmaceutically acceptable carriers or pharmaceutically acceptable excipients. Such carriers are well known to those skilled in the art. For example, injectable drug delivery systems include solutions, suspensions, gels, microspheres and polymeric injectables, and can include excipients such as solubility-altering agents (e.g., ethanol, propylene glycol and sucrose) and polymers (e.g., polycaprylactones and PLGA's). An exemplary formulation may be as substantially described in U.S. Pat. No. 10,420, 851 or International Pub. No. WO 2017/155937, incorporated by reference herein. For example, according to certain aspects, the formulation may include 0.5% to 5.0% (w/v) of an excipient selected from the group consisting of ascorbic acid, polyvinylpyrrolidone (PVP), human serum albumin (HSA), a water-soluble salt of HSA, and mixtures thereof. Certain formulations may include 0.5-5% ascorbic acid; 0.54% polyvinylpyrrolidone (PVP); and the monoclonal antibody in 50 mM PBS buffer, pH 7.

The anti-hCalreticulin nanobodies and nanobody fusion proteins disclosed herein may, for example, be labeled with radionuclide, such as $^{131}$I, $^{177}$Lu, or $^{225}$Ac, or conjugated to a cytotoxic drug, for use in the treatment of a Calreticulin-expressing cancer such as a breast cancer.

Cancers, including precancerous conditions that may be treated or imaged using proteins or conjugates thereof that include one or more of the anti-hCRT nanobodies disclosed herein include hematological ("liquid") cancers and precancerous disorders and solid tumor cancer and precancerous disorders.

The hematological cancer or precancer may, for example, include a leukemia (such as acute myeloid leukemia (AML), acute promyelocytic leukemia, acute lymphoblastic leukemia (ALL), acute mixed lineage leukemia, chronic myeloid leukemia (CML), chronic lymphocytic leukemia (CLL), hairy cell leukemia, or large granular lymphocytic leukemia), myelodysplastic syndrome (MDS), a myeloproliferative disorders (polycythemia vera, essential thrombocytosis, primary myelofibrosis and chronic myeloid leukemia), multiple myeloma, MGUS and similar disorders, a lymphoma, Hodgkin lymphoma (HL), non-Hodgkin lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, T-cell lymphoma, and other B-cell malignancies.

The solid cancer or solid precancerous conditions may, for example, include a bone cancer, pancreatic cancer, skin cancer, cutaneous or intraocular malignant melanoma, uterine cancer, ovarian cancer, cancer of the anal region, stomach cancer, gastric cancer, testicular cancer, uterine cancer, carcinoma of the fallopian tubes, endometrial cancer, carcinoma of the endometrium, cervical cancer, carcinoma of the cervix, cervical epidermoid cancer, carcinoma of the vagina, carcinoma of the vulva, esophageal cancer, bronchioloalveolar cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, cancer of lung such as non-small cell lung carcinoma (NSCLC) or small cell lung carcinoma (SCLC), carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos such as mesothelioma, a breast cancer such as metastatic breast cancer, tamoxifen-sensitive breast cancer, tamoxifen-resistant breast cancer or triple negative breast cancer (TNBC), bladder cancer, prostate cancer such as castration resistant prostate cancer (CRPC), metastatic prostate cancer or metastatic CRPC (mCRPC), colorectal cancer, liver cancer such as hepatocellular carcinoma (HCC) or cholangiocarcinoma, renal cell carcinoma, head and neck cancer such as head and neck squamous cell cancer, a carcinoma, a sarcoma, or any combination thereof.

In general, the various aspects of the invention may be employed in the treatment and/or imaging of non-metastatic, premetastatic, and metastatic forms of cancers such as any of the aforementioned cancers.

Without limitation, the following aspects of the invention are also provided.

Aspect 1. A protein including a human-calreticulin binding nanobody amino acid sequence including the CDR1, CDR2, and CDR3 amino acid sequences of any one of the nanobody amino acid sequences set forth in SEQ ID NOS:72-134.

Aspect 2. The protein of aspect 1, including a human-calreticulin binding nanobody amino acid sequence including the CDR1, CDR2, and CDR3 sequences:

(i) SEQ ID NO:18, SEQ ID NO: 41, and SEQ ID NO:60, respectively;

(ii) SEQ ID NO:21, SEQ ID NO: 44, and SEQ ID NO:63, respectively;

(iii) SEQ ID NO:26, SEQ ID NO:49, and SEQ ID NO:68, respectively;

(iv) SEQ ID NO:22, SEQ ID NO:45, and SEQ ID NO:64, respectively;

(v) SEQ ID NO:14, SEQ ID NO:39, and SEQ ID NO:58, respectively;

(vi) SEQ ID NO:11, SEQ ID NO:35, and SEQ ID NO:57, respectively;

(vii) SEQ ID NO:20, SEQ ID NO:43, and SEQ ID NO:62, respectively; or (viii) SEQ ID NO:19, SEQ ID NO: 42, and SEQ ID NO:61, respectively.

Aspect 3. The protein of aspect 1, including one or more of the human-calreticulin binding nanobody amino acid sequences set forth in SEQ ID NOS:72-134.

Aspect 4. The protein of aspect 3, including one or more of the human-calreticulin binding nanobody amino acid sequences set forth in SEQ ID NOS:120, 126, 131, 127, 115, 111, 125 or 123.

Aspect 5. The protein of any one of aspects 1-4, consisting of a single VHH domain.

Aspect 6. The protein of any one of aspects 1-4, wherein the protein is a nanobody Fc fusion protein.

Aspect 7. A pharmaceutical composition including the protein of any one of aspects 1-6 and at least pharmaceutically acceptable excipient.

Aspect 8. A radiopharmaceutical composition including the protein of any one of aspects 1-6 linked to a radionuclide.

Aspect 9. The radiopharmaceutical composition of aspect 8, further including at least one pharmaceutically acceptable excipient.

Aspect 10. The radiopharmaceutical composition of aspect 9 or 10, wherein the radionuclide is an alpha particle emitter.

Aspect 11. The radiopharmaceutical composition of aspect 9 or 10, wherein the radionuclide is a beta particle emitter.

Aspect 12. The radiopharmaceutical composition of aspect 9 or 10, wherein the radionuclide includes $^{131}$I.

Aspect 13. The radiopharmaceutical composition of aspect 9 or 10, wherein the radionuclide includes $^{225}$Ac, $^{177}$Lu or $^{90}$Y.

Aspect 14 A composition including the protein of any one of aspects 1-6, chemically conjugated to a chelator.

Aspect 15. The composition of aspect 14, wherein the chelator includes DOTA or a DOTA derivative.

Aspect 16. The composition of aspect 14 or 15, further including a radionuclide chelated by the chelator.

Example 1: Production of a Radiolabeled Anti-hCalreticulin Nanobody

The following exemplary procedures may be used to conjugate an anti-hCRT nanobody as disclosed herein to the chelator DOTA and label the conjugate with $^{225}$Ac.

Conjugation to a chelator: 23 µl of p-SCN-Bn-DOTA 20 mg/ml solution (in deionized water) is added to a 1.5 ml Eppendorf tube containing 1 mg anti-hCRT nanobody in 0.2 ml 0.1M NaHCO3 solution, and the total volume brought to 0.3 ml with 0.1M NaHCO3. The reaction mixture is then incubated at 37° C. for 2 hours with agitation. HPLC analysis of the reaction mixture can then performed; 10 µl sample is mixed with 50 µl water, and 50 µl is injected into the HPLC apparatus. The resulting conjugate may be purified using a 10K Pierce® protein concentrator (Thermo Scientific) with 0.25M NaOAc at 8000G at 4° C.

Radiolabeling: Once the nanobody (or nanobody fusion protein) has been conjugated to a chelator, such as DOTA as described above, it may be labeled with a radionuclide such as $^{177}$Lu, $^{90}$Y, or $^{225}$Ac.

An exemplary labeling reaction for $^{225}$Ac is as follows: a reaction including 15 µl 0.15M NH$_4$OAc buffer, pH=6.5 and 2 µL (10 µg) DOTA-anti-hCRT nanobody (5 mg/ml) may be mixed in an Eppendorf reaction tube, and 4 µL $^{225}$Ac (10 Ci) in 0.05 M HCl subsequently added. The contents of the tube may be mixed with a pipette tip and the reaction mixture incubated at 37° C. for 90 min with shaking at 100 rpm. At the end of the incubation period, 3 µL of a 1 mM DTPA solution may be added to the reaction mixture and incubated at room temperature for 20 min to bind the unreacted $^{225}$Ac into the $^{225}$Ac-DTPA complex. Instant thin layer chromatography with 10 cm silica gel strip and 10 mM EDTA/normal saline mobile phase may be used to determine the radiochemical purity of $^{225}$Ac-DOTA-anti-hCRT-nanobody through separating $^{225}$Ac-labeled DOTA-conjugated nanobody from free $^{225}$Ac ($^{225}$Ac-DTPA). In this system, the radiolabeled antibody stays at the point of application and $^{225}$Ac-DTPA moves with the solvent front. The strips may be cut in halves and counted in the gamma counter equipped with the multichannel analyzer using channels 72-110 for $^{225}$Ac to exclude its daughters.

Purification: Radiolabeled nanobody may, for example, be purified using Pierce R protein concentrators PES, 3K MWCO volume 0.5 mL (Thermo Scientific) and 2-6 mL buffer solution. An exemplary radiolabeled targeting agent, such as 225Ac-DOTA-nanobody Fc fusion protein, may be purified either on PD10 columns pre-blocked with 1% HSA or on Vivaspin® centrifugal concentrators with a 50 kDa MW cut-off with 2×1.5 mL washes, 3 min per spin. HPLC analyses of the 225Ac-DOTA-antibody after purification may be conducted using a Waters HPLC system equipped with flow-through Waters UV and Bioscan Radiation detectors, using a TSK3000SW XL column eluted with PBS at pH=7.4 and a flow rate of 1 ml/min. Appropriate molecular weight cutoff filters are readily selectable and available for the purification of subject radiolabeled proteins of different molecular weights.

Example 2: Generation of the Anti-hCRT Nanobodies

The methods used to generate the anti-hCRT nanobodies of this disclosure are described below.

Immunizations with Recombinant Human Calreticulin

Two llamas were subcutaneously injected on days 0, 14, 28, 42, 70 and 84, each time & per animal with about 100 to 150 µg of recombinant human Calreticulin (amino acids 18-417; Cat. No. NBP1-44499, Novus Biologicals, LLC, Centennial, Colorado, USA). A His$_6$ tag is present at the N-terminus of this protein. The adjuvant used was Gerbu adjuvant P. On day 87 (3 d.p.i) and on day 91 (7 d.p.i), about 100 ml anticoagulated blood was collected from each llama for lymphocyte preparation. Animal health was regularly monitored. None of the animals showed any sign of discomfort during the whole immunization period.

Construction of Two Independent VHH Libraries

Individual VHH libraries were constructed from each llama's lymphocytes to screen for the presence of antigen-specific Nanobodies (Nbs). To this end, a mix (ratio of 1:1) of total RNA from peripheral blood lymphocytes from 3 d.p.i. & 7 d.p.i. was used as template for first strand cDNA synthesis with an oligo(dT) primer. Using this cDNA, the VHH encoding sequences were amplified by PCR. For each llama, PCR fragments were digested with SapI, and cloned into the SapI site of the phagemid vector pMECS-GG. The VHH library obtained from the first animal was called Core 178B. The Core 178B library consists of about 5×10$^8$ independent transformants, with about 92% of transformants harboring the vector with the right insert size of VHH-encoding sequences. The library obtained from the second animal, Core 179B, also consists of about $5×10^8$ independent transformants, with about 92% of transformants harboring the vector with the right insert size.

Isolation of Human Calreticulin-Specific Nanobodies

Both libraries were separately panned on solid-phase coated recombinant human Calreticulin with an N-terminal $His_6$ tag (100 µg/ml in 100 mM $NaHCO_3$ pH 8.2) for 3 rounds. The enrichment for antigen-specific phages was assessed after each round of panning by comparing the number of phagemid particles eluted from antigen-coated wells with the number of phagemid particles eluted from negative control (uncoated blocked) wells.

For Core 178B, these experiments suggested that the phage population was enriched for antigen-specific phages about 1.5-fold, 15-fold and 40-fold after the $1^{st}$, $2^{nd}$ and $3^{rd}$ round, respectively. In total, 380 colonies (190 from round 2, 190 from round 3) were randomly selected and analyzed by ELISA for the presence of antigen-specific nanobodies in their periplasmic extracts (ELISA using crude periplasmic extracts including soluble Nanobodies). The antigen used for panning & ELISA screening was the same one as used for immunization, using uncoated blocked wells as negative controls (blank). Out of the 380 colonies tested by ELISA, 264 colonies scored positive for human Calreticulin. Based on sequence data of the 264 positive colonies, 22 different Nanobodies were identified, belonging to 4 different CDR3 groups (B-cell lineages) (see Excel file). Nanobodies belonging to the same CDR3 group (same B-cell lineage) are very similar and their amino acid sequences suggest that they are from clonally-related B-cells resulting from somatic hypermutation or from the same B-cell but diversified due to RT and/or PCR error during library construction. Nanobodies belonging to the same CDR3 group recognize the same epitope but their other characteristics (e.g. affinity, potency, stability, expression yield, etc.) can be different. Nanobodies resulting from the panning/ELISA screening of the Core 178B library bear "TIC" in their names.

When panning the Core 179B library on human Calreticulin, the enrichment experiments suggested that the phage population was enriched for antigen-specific phages about 25-fold and 60-fold after the $2^{nd}$ and $3^{rd}$ round, respectively. No enrichment was observed during the $1^{st}$ round. Here also, in total 380 colonies (190 from round 2, 190 from round 3) were randomly selected and analyzed by ELISA for the presence of antigen-specific nanobodies in their periplasmic extracts, as described above. Out of the 380 colonies tested by ELISA, 245 colonies scored positive for human Calreticulin. Based on sequence data of the 245 positive colonies, 41 different nanobodies were identified, belonging to 11 different CDR3 groups (B-cell lineages). Nanobodies resulting from the panning/ELISA screening of the Core 179B library bear "SPC" in their names.

In summary, sixty-three (63) unique human Calreticulin-specific nanobodies (SEQ ID NOS:72-134) belonging to 15 different CDR3 groups were identified. The VHH and CDR sequences for these nanobody clones are presented in FIGS. 1A-1C.

While various specific embodiments have been illustrated and described herein, it will be appreciated that various changes can be made without departing from the spirit and scope of the invention(s). Moreover, features described in connection with one aspect of the invention may be used in conjunction with other aspects of the invention, even if not explicitly exemplified in combination within.

What is claimed is:

1. A protein comprising a human-calreticulin binding nanobody amino acid sequence comprising the CDR1, CDR2, and CDR3 sequences:
    (i) SEQ ID NO:18, SEQ ID NO: 41, and SEQ ID NO:60, respectively;
    (ii) SEQ ID NO:21, SEQ ID NO: 44, and SEQ ID NO:63, respectively;
    (iii) SEQ ID NO:26, SEQ ID NO:49, and SEQ ID NO:68, respectively;
    (iv) SEQ ID NO:22, SEQ ID NO:45, and SEQ ID NO:64, respectively;
    (v) SEQ ID NO:14, SEQ ID NO:39, and SEQ ID NO:58, respectively;
    (vi) SEQ ID NO:20, SEQ ID NO:43, and SEQ ID NO:62, respectively; or
    (vii) SEQ ID NO:19, SEQ ID NO: 42, and SEQ ID NO:61, respectively.

2. A protein comprising one or more of the human-calreticulin binding nanobody amino acid sequences set forth in SEQ ID NOS: 120, 126, 131, 127, 115, 111, 125 or 123.

3. The protein of claim 2, comprising the human-calreticulin binding nanobody amino acid sequence set forth in SEQ ID NO: 120.

4. The protein of claim 1, consisting of a single VHH domain.

5. The protein of claim 1, wherein the protein is a nanobody Fc fusion protein.

6. A pharmaceutical composition comprising the protein of claim 1 and at least one pharmaceutically acceptable excipient.

7. A radiopharmaceutical composition comprising the protein of claim 1 linked to a radionuclide.

8. The radiopharmaceutical composition of claim 7, further comprising at least one pharmaceutically acceptable excipient.

9. The radiopharmaceutical composition of claim 8, wherein the radionuclide is an alpha particle emitter.

10. The radiopharmaceutical composition of claim 8, wherein the radionuclide is a beta particle emitter.

11. The radiopharmaceutical composition of claim 8, wherein the radionuclide comprises $^{131}$I.

12. The radiopharmaceutical composition of claim 8, wherein the radionuclide comprises $^{225}$Ac, $^{177}$Lu or $^{90}$Y.

13. A composition comprising the protein of claim 1, chemically conjugated to a chelator.

14. The composition of claim 13, wherein the chelator comprises DOTA or a DOTA derivative.

15. The composition of claim 13, further comprising a radionuclide chelated by the chelator.

16. The protein of claim 2, consisting of a single VHH domain.

17. The protein of claim 2, wherein the protein is a nanobody Fc fusion protein.

18. A pharmaceutical composition comprising the protein of claim 2 and at least one pharmaceutically acceptable excipient.

19. A radiopharmaceutical composition comprising the protein of claim 2 linked to a radionuclide.

20. A radiopharmaceutical composition comprising the protein of claim 3 linked to a radionuclide.

21. The protein of claim 1, comprising a human-calreticulin binding nanobody amino acid sequence comprising the CDR1, CDR2, and CDR3 sequences:
    SEQ ID NO:18, SEQ ID NO: 41, and SEQ ID NO:60, respectively.

* * * * *

SEQUENCE LISTING

```
Sequence total quantity: 142
SEQ ID NO: 1              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 1
GITFRNSW                                                          8

SEQ ID NO: 2              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 2
GSIMSSYQ                                                          8

SEQ ID NO: 3              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 3
GITFRSSW                                                          8

SEQ ID NO: 4              moltype = AA  length = 8
FEATURE                   Location/Qualifiers
REGION                    1..8
                          note = nanobody component sequence
```

-continued

```
source                    1..8
                          mol_type = protein
                          organism = synthetic construct
SEQUENCE: 4
DITFRNSW                                                          8

SEQ ID NO: 5              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 5
GITFRSTW                                                          8

SEQ ID NO: 6              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 6
GTTFSNYW                                                          8

SEQ ID NO: 7              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 7
GFTFSNYR                                                          8

SEQ ID NO: 8              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 8
GVTFRSSW                                                          8

SEQ ID NO: 9              moltype = AA  length = 8
FEATURE                   Location/Qualifiers
REGION                    1..8
                          note = nanobody component sequence
source                    1..8
                          mol_type = protein
                          organism = synthetic construct
SEQUENCE: 9
GINFRNSW                                                          8

SEQ ID NO: 10             moltype = AA  length = 8
FEATURE                   Location/Qualifiers
REGION                    1..8
                          note = nanobody component sequence
source                    1..8
                          mol_type = protein
                          organism = synthetic construct
SEQUENCE: 10
GFMFSRHW                                                          8

SEQ ID NO: 11             moltype = AA  length = 8
FEATURE                   Location/Qualifiers
REGION                    1..8
                          note = nanobody component sequence
source                    1..8
                          mol_type = protein
                          organism = synthetic construct
SEQUENCE: 11
NFLSSRFE                                                          8

SEQ ID NO: 12             moltype = AA  length = 8
FEATURE                   Location/Qualifiers
REGION                    1..8
```

```
                          note = nanobody component sequence
source                    1..8
                          mol_type = protein
                          organism = synthetic construct
SEQUENCE: 12
NLLSSRFE                                                              8

SEQ ID NO: 13             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 13
NFLNSRFE                                                              8

SEQ ID NO: 14             moltype = AA   length = 8
FEATURE                   Location/Qualifiers
REGION                    1..8
                          note = nanobody component sequence
source                    1..8
                          mol_type = protein
                          organism = synthetic construct SEQUENCE: 14
GFVFSNYA                                                              8

SEQ ID NO: 15             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 15
GFTFSAYA                                                              8

SEQ ID NO: 16             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 16
GFAFSDYH                                                              8

SEQ ID NO: 17             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 17
GSTLDYYA                                                              8

SEQ ID NO: 18             moltype = AA   length = 5
FEATURE                   Location/Qualifiers
REGION                    1..5
                          note = nanobody component sequence
source                    1..5
                          mol_type = protein
                          organism = synthetic construct
SEQUENCE: 18
GSIAA                                                                 5

SEQ ID NO: 19             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 19
GRMNTRTA                                                              8

SEQ ID NO: 20             moltype = AA   length = 8
FEATURE                   Location/Qualifiers
```

```
REGION                    1..8
                          note = nanobody component sequence
source                    1..8
                          mol_type = protein
                          organism = synthetic construct
SEQUENCE: 20
NVMFSRFT                                                                    8

SEQ ID NO: 21             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 21
TFPFTMNN                                                                    8

SEQ ID NO: 22             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 22
SSAFSLTP                                                                    8

SEQ ID NO: 23             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 23
GFTFSSYQ                                                                    8

SEQ ID NO: 24             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 24
GSILRINT                                                                    8

SEQ ID NO: 25             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 25
GGAFTTYS                                                                    8

SEQ ID NO: 26             moltype = AA   length = 8
FEATURE                   Location/Qualifiers
REGION                    1..8
                          note = nanobody component sequence
source                    1..8
                          mol_type = protein
                          organism = synthetic construct
SEQUENCE: 26
GGTFSNYG                                                                    8

SEQ ID NO: 27             moltype = AA   length = 13
FEATURE                   Location/Qualifiers
REGION                    1..13
                          note = nanobody component sequence
source                    1..13
                          mol_type = protein
                          organism = synthetic construct
SEQUENCE: 27
GRTFSYSAMG GDV                                                              13

SEQ ID NO: 28             moltype = AA   length = 8
```

-continued

| FEATURE | Location/Qualifiers |
|---------|---------------------|
| REGION | 1..8 |
| | note = nanobody component sequence |
| source | 1..8 |
| | mol_type = protein |
| | organism = synthetic construct |

SEQUENCE: 28
GGTLSSYA                                                                                    8

| SEQ ID NO: 29 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 29
GRTSSRYA                                                                                    8

| SEQ ID NO: 30 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 30
ISDGGGTT                                                                                    8

| SEQ ID NO: 31 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 31
ISEAGYTQ                                                                                    8

| SEQ ID NO: 32 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 32
ISESGGTT                                                                                    8

| SEQ ID NO: 33 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 33
INESGGTT                                                                                    8

| SEQ ID NO: 34 | moltype = AA   length = 8 |
|---------------|---------------------------|
| FEATURE | Location/Qualifiers |
| REGION | 1..8 |
| | note = nanobody component sequence |
| source | 1..8 |
| | mol_type = protein |
| | organism = synthetic construct |

SEQUENCE: 34
INESGGTA                                                                                    8

| SEQ ID NO: 35 | moltype = AA   length = 7 |
|---------------|---------------------------|
| FEATURE | Location/Qualifiers |
| REGION | 1..7 |
| | note = nanobody component sequence |
| source | 1..7 |
| | mol_type = protein |
| | organism = synthetic construct |

SEQUENCE: 35
IFRDGNT                                                                                     7

```
SEQ ID NO: 36        moltype = AA   length = 7
FEATURE              Location/Qualifiers
REGION               1..7
                     note = nanobody component sequence
source               1..7
                     mol_type = protein
                     organism = synthetic construct
SEQUENCE: 36
IFRDENT                                                              7

SEQ ID NO: 37        moltype = AA   length = 7
FEATURE              Location/Qualifiers
REGION               1..7
                     note = nanobody component sequence
source               1..7
                     mol_type = protein
                     organism = synthetic construct
SEQUENCE: 37
IFRDGMT                                                              7

SEQ ID NO: 38        moltype = AA   length = 7
FEATURE              Location/Qualifiers
REGION               1..7
                     note = nanobody component sequence
source               1..7
                     mol_type = protein
                     organism = synthetic construct
SEQUENCE: 38
IFRDGTT                                                              7

SEQ ID NO: 39        moltype = AA   length = 8
FEATURE              Location/Qualifiers
REGION               1..8
                     note = nanobody component sequence
source               1..8
                     mol_type = protein
                     organism = synthetic construct
SEQUENCE: 39
ITNSGSTT                                                             8

SEQ ID NO: 40        moltype = AA   length = 8
FEATURE              Location/Qualifiers
REGION               1..8
                     note = nanobody component sequence
source               1..8
                     mol_type = protein
                     organism = synthetic construct
SEQUENCE: 40
ITNTGTTT                                                             8

SEQ ID NO: 41        moltype = AA   length = 7
FEATURE              Location/Qualifiers
REGION               1..7
                     note = nanobody component sequence
source               1..7
                     mol_type = protein
                     organism = synthetic construct
SEQUENCE: 41
MYVGGSI                                                              7

SEQ ID NO: 42        moltype = AA   length = 8
FEATURE              Location/Qualifiers
REGION               1..8
                     note = nanobody component sequence
source               1..8
                     mol_type = protein
                     organism = synthetic construct
SEQUENCE: 42
IDWTGDST                                                             8

SEQ ID NO: 43        moltype = AA   length = 7
FEATURE              Location/Qualifiers
REGION               1..7
                     note = nanobody component sequence
source               1..7
                     mol_type = protein
                     organism = synthetic construct
SEQUENCE: 43
IARDGMT                                                              7
```

-continued

```
SEQ ID NO: 44          moltype = AA  length = 7
FEATURE                Location/Qualifiers
REGION                 1..7
                       note = nanobody component sequence
source                 1..7
                       mol_type = protein
                       organism = synthetic construct
SEQUENCE: 44
ITNDGSI                                                             7

SEQ ID NO: 45          moltype = AA  length = 7
FEATURE                Location/Qualifiers
REGION                 1..7
                       note = nanobody component sequence
source                 1..7
                       mol_type = protein
                       organism = synthetic construct
SEQUENCE: 45
ITTGSTV                                                             7

SEQ ID NO: 46          moltype = AA  length = 8
FEATURE                Location/Qualifiers
REGION                 1..8
                       note = nanobody component sequence
source                 1..8
                       mol_type = protein
                       organism = synthetic construct
SEQUENCE: 46
ISTNGGII                                                            8

SEQ ID NO: 47          moltype = AA  length = 7
FEATURE                Location/Qualifiers
REGION                 1..7
                       note = nanobody component sequence
source                 1..7
                       mol_type = protein
                       organism = synthetic construct
SEQUENCE: 47
ITSGGRP                                                             7

SEQ ID NO: 48          moltype = AA  length = 7
FEATURE                Location/Qualifiers
REGION                 1..7
                       note = nanobody component sequence
source                 1..7
                       mol_type = protein
                       organism = synthetic construct
SEQUENCE: 48
INKSGKT                                                             7

SEQ ID NO: 49          moltype = AA  length = 8
FEATURE                Location/Qualifiers
REGION                 1..8
                       note = nanobody component sequence
source                 1..8
                       mol_type = protein
                       organism = synthetic construct
SEQUENCE: 49
INWSGAIT                                                            8

SEQ ID NO: 50          moltype = AA  length = 8
FEATURE                Location/Qualifiers
REGION                 1..8
                       note = nanobody component sequence
source                 1..8
                       mol_type = protein
                       organism = synthetic construct
SEQUENCE: 50
ISGSGAST                                                            8

SEQ ID NO: 51          moltype = AA  length = 8
FEATURE                Location/Qualifiers
REGION                 1..8
                       note = nanobody component sequence
source                 1..8
                       mol_type = protein
                       organism = synthetic construct
SEQUENCE: 51
```

-continued

```
ISRTDGRT                                                            8

SEQ ID NO: 52          moltype = AA  length = 8
FEATURE                Location/Qualifiers
REGION                 1..8
                       note = nanobody component sequence
source                 1..8
                       mol_type = protein
                       organism = synthetic construct
SEQUENCE: 52
VSFSGDST                                                            8

SEQ ID NO: 53          moltype = AA  length = 8
FEATURE                Location/Qualifiers
REGION                 1..8
                       note = nanobody component sequence
source                 1..8
                       mol_type = protein
                       organism = synthetic construct
SEQUENCE: 53
STDMHGTG                                                            8

SEQ ID NO: 54          moltype = AA  length = 8
FEATURE                Location/Qualifiers
REGION                 1..8
                       note = nanobody component sequence
source                 1..8
                       mol_type = protein
                       organism = synthetic construct
SEQUENCE: 54
ATDMTGTG                                                            8

SEQ ID NO: 55          moltype = AA  length = 8
FEATURE                Location/Qualifiers
REGION                 1..8
                       note = nanobody component sequence
source                 1..8
                       mol_type = protein
                       organism = synthetic construct
SEQUENCE: 55
STDTHGTG                                                            8

SEQ ID NO: 56          moltype = AA  length = 8
FEATURE                Location/Qualifiers
REGION                 1..8
                       note = nanobody component sequence
source                 1..8
                       mol_type = protein
                       organism = synthetic construct
SEQUENCE: 56
STDMHGTD                                                            8

SEQ ID NO: 57          moltype = AA  length = 9
FEATURE                Location/Qualifiers
REGION                 1..9
                       note = nanobody component sequence
source                 1..9
                       mol_type = protein
                       organism = synthetic construct
SEQUENCE: 57
HVHILGRDY                                                           9

SEQ ID NO: 58          moltype = AA  length = 17
FEATURE                Location/Qualifiers
REGION                 1..17
                       note = nanobody component sequence
source                 1..17
                       mol_type = protein
                       organism = synthetic construct
SEQUENCE: 58
GAVEPGAGLG ASRDLLY                                                  17

SEQ ID NO: 59          moltype = AA  length = 17
FEATURE                Location/Qualifiers
REGION                 1..17
                       note = nanobody component sequence
source                 1..17
                       mol_type = protein
                       organism = synthetic construct
```

```
SEQUENCE: 59
AAVKPGHGLG ASRELLY                                                          17

SEQ ID NO: 60          moltype = AA  length = 13
FEATURE                Location/Qualifiers
REGION                 1..13
                       note = nanobody component sequence
source                 1..13
                       mol_type = protein
                       organism = synthetic construct
SEQUENCE: 60
NALVRFEGRN DDY                                                              13

SEQ ID NO: 61          moltype = AA  length = 19
FEATURE                Location/Qualifiers
REGION                 1..19
                       note = nanobody component sequence
source                 1..19
                       mol_type = protein
                       organism = synthetic construct
SEQUENCE: 61
SDTSYGALRV HTAPSEYEH                                                        19

SEQ ID NO: 62          moltype = AA  length = 9
FEATURE                Location/Qualifiers
REGION                 1..9
                       note = nanobody component sequence
source                 1..9
                       mol_type = protein
                       organism = synthetic construct
SEQUENCE: 62
NCQILGRDY                                                                    9

SEQ ID NO: 63          moltype = AA  length = 9
FEATURE                Location/Qualifiers
REGION                 1..9
                       note = nanobody component sequence
source                 1..9
                       mol_type = protein
                       organism = synthetic construct
SEQUENCE: 63
NRGTGPSYP                                                                    9

SEQ ID NO: 64          moltype = AA  length = 13
FEATURE                Location/Qualifiers
REGION                 1..13
                       note = nanobody component sequence
source                 1..13
                       mol_type = protein
                       organism = synthetic construct
SEQUENCE: 64
NRIYIGDTFP PWN                                                              13

SEQ ID NO: 65          moltype = AA  length = 13
FEATURE                Location/Qualifiers
REGION                 1..13
                       note = nanobody component sequence
source                 1..13
                       mol_type = protein
                       organism = synthetic construct
SEQUENCE: 65
ARCDVAYWSD SCD                                                              13

SEQ ID NO: 66          moltype = AA  length = 15
FEATURE                Location/Qualifiers
REGION                 1..15
                       note = nanobody component sequence
source                 1..15
                       mol_type = protein
                       organism = synthetic construct
SEQUENCE: 66
NVYARLTGSD SYLAY                                                            15

SEQ ID NO: 67          moltype = AA  length = 17
FEATURE                Location/Qualifiers
REGION                 1..17
                       note = nanobody component sequence
source                 1..17
                       mol_type = protein
```

-continued

```
                                organism = synthetic construct
SEQUENCE: 67
AASVADGVFV GTNMYHY                                                          17

SEQ ID NO: 68        moltype = AA  length = 19
FEATURE              Location/Qualifiers
REGION               1..19
                     note = nanobody component sequence
source               1..19
                     mol_type = protein
                     organism = synthetic construct
SEQUENCE: 68
AAVTRYGGYA DSRPQWYDS                                                        19

SEQ ID NO: 69        moltype = AA  length = 20
FEATURE              Location/Qualifiers
REGION               1..20
                     note = nanobody component sequence
source               1..20
                     mol_type = protein
                     organism = synthetic construct
SEQUENCE: 69
AAAPRTYYGT NYRNKGEYDY                                                       20

SEQ ID NO: 70        moltype = AA  length = 22
FEATURE              Location/Qualifiers
REGION               1..22
                     note = nanobody component sequence
source               1..22
                     mol_type = protein
                     organism = synthetic construct
SEQUENCE: 70
AAGMGVSAYS SGGYFNAERY DY                                                    22

SEQ ID NO: 71        moltype = AA  length = 22
FEATURE              Location/Qualifiers
REGION               1..22
                     note = nanobody component sequence
source               1..22
                     mol_type = protein
                     organism = synthetic construct
SEQUENCE: 71
ASRPPGPAYS DTAYSRAYEY NY                                                    22

SEQ ID NO: 72        moltype = AA  length = 115
FEATURE              Location/Qualifiers
REGION               1..115
                     note = nanobody component sequence
source               1..115
                     mol_type = protein
                     organism = synthetic construct
SEQUENCE: 72
QVQLQESGGG LVRPGGSLLL SCKASGITFR NSWMYWVRQA PGQGLEWVSG ISDGGGTTKS  60
NNFVNGRFSI FRDNAWNVVY LHMHDLKSED SAVYYCSTDM HGTGRGQGTQ VTVSS       115

SEQ ID NO: 73        moltype = AA  length = 115
FEATURE              Location/Qualifiers
REGION               1..115
                     note = nanobody component sequence
VARIANT              33
                     note = misc_feature - Xaa can be any naturally occurring
                      amino acid
source               1..115
                     mol_type = protein
                     organism = synthetic construct
SEQUENCE: 73
QVQLQESGGG LVQPGGSLTL SCVASGSIMS SYXMYWVRQA PEKGLEWVSG ISEAGYTQKY  60
NNFVKGRFTI SRDNAKNMVY LHMTGLKFED TAVYYCATDM TGTGRGQGTQ VTVSS       115

SEQ ID NO: 74        moltype = AA  length = 115
FEATURE              Location/Qualifiers
REGION               1..115
                     note = nanobody component sequence
source               1..115
                     mol_type = protein
                     organism = synthetic construct
SEQUENCE: 74
QVQLQESGGG LVQPGGSLRL SCKASGITFR NSWMYWVRQA PGQGLEWVSG ISESGGTTKS  60
NNFVNGRFSI FRDNAWNVVY LHMHDLKSED SAMYYCSTDM HGTGRGQGTQ VTVSS       115
```

-continued

```
SEQ ID NO: 75              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 75
QVQLQESGGG LVRPGRSLLL SCKASGITFR SSWMYWVRQA PGQGLEWVSG INESGGTTKS   60
NNFVNGRFSI FRDNAWNVVY LHMHDLKSED SAMYYCSTDM HGTGRGQGTQ VTVSS       115

SEQ ID NO: 76              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 76
QVQLQESGGG LVRPGGSLLL SCKASGITFR NSWMYWVRQA PGQGLEWVSG ISESGGTTKS   60
NNFVNGRFSI FRDNAWNVVY LHMHDLKSED SAMYYCSTDM HGTGRGQGTQ VTVSS       115

SEQ ID NO: 77              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 77
QVQLQESGGG LVRPGGSLLL SCKASDITFR NSWMYWVRQA PGQGLEWVSG ISESGGTTKS   60
NNFVNGRFSI FRDNAWNVVY LHMHDLKSED SAMYYCSTDT HGTGRGQGTQ VTVSS       115

SEQ ID NO: 78              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 78
QVQLQESGGG LVRPGRSLLL SCKASGITFR NSWMYWVRQA PGQGLEWVSG ISESGGTTKS   60
NNFVNGRFSI FRDNAWNVVY LHMHDLKSED SAMYYCSTDM HGTGRGQGTQ VTVSS       115

SEQ ID NO: 79              moltype = AA  length = 115
FEATURE                    Location/Qualifiers
REGION                     1..115
                           note = nanobody component sequence
VARIANT                    36
                           note = misc_feature - Xaa can be any naturally occurring
                            amino acid
source                     1..115
                           mol_type = protein
                           organism = synthetic construct
SEQUENCE: 79
QVQLQESGGG LVRPGGSLLL SCKASGITFR STWMYXVRQA PGQGLEWVSG INESGGTTKS   60
NNFVSGRFSI FRDNAWNVVY LHMHDLKSED SAMYYCSTDM HGTGRGQGTQ VTVSS       115

SEQ ID NO: 80              moltype = AA  length = 115
FEATURE                    Location/Qualifiers
REGION                     1..115
                           note = nanobody component sequence
VARIANT                    76
                           note = misc_feature - Xaa can be any naturally occurring
                            amino acid
source                     1..115
                           mol_type = protein
                           organism = synthetic construct
SEQUENCE: 80
QVQLQESGGG LVQPGGSLRL SCAASGTTFS NYWMYWIRQA PGQGLEWVSG ISESGGTTKS   60
NNFVNGRFSI FRDNAXNVVY LHMHDLKSED SAMYYCSTDM HGTGRGQGTQ VTVSS       115

SEQ ID NO: 81              moltype = AA  length = 115
FEATURE                    Location/Qualifiers
REGION                     1..115
                           note = nanobody component sequence
source                     1..115
                           mol_type = protein
```

-continued

```
                          organism = synthetic construct
SEQUENCE: 81
QVQLQESGGG LVRPGGSLLL SCKASDITFR NSWMYWVRQA PGQGLEWVSG ISESGGTTKS   60
NNFVNGRFSI FRDNAWNVVY LHMHDLKSED SAMYYCSTDM HGTGRGQGTQ VTVSS       115

SEQ ID NO: 82           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 82
QVQLQESGGG LVRPGGSLLL SCKASGITFR SSWMYWVRQA PGQGLEWVSG INESGGTTKS   60
NNFVNGRFSI FRDNAWNVVY LHMHDLKSED SAMYYCSTDM HGTGRGQGTQ VTVSS       115

SEQ ID NO: 83           moltype = AA   length = 115
FEATURE                 Location/Qualifiers
REGION                  1..115
                        note = nanobody component sequence
VARIANT                 13
                        note = misc_feature - Xaa can be any naturally occurring
                         amino acid
source                  1..115
                        mol_type = protein
                        organism = synthetic construct
SEQUENCE: 83
QVQLQESGGG LVXPGGSLKL SCTASGFTFS NYRMYWVRQA PEKGLEWVSG ISEAGYTQKY   60
NNFVKGRFTI SRDNAKNMVY LHMTGLKFED TAVYYCATDM TGTGRGQGTQ VTVSS       115

SEQ ID NO: 84           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 84
QVQLQESGGG LVRPGGSLLL SCKASDITFR NSWMYWVRQA PGQGLEWVSG ISESGGTTKS   60
NNFVNGRFSI FRDNAWNVVY LHMHDLKSED SAIYYCSTDM HGTGRGQGTQ VTVSS       115

SEQ ID NO: 85           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 85
QVQLQESGGG LVRPGGSLLL SCKASGITFR STWMYWVRQA PGQGLEWVSG INESGGTTKS   60
NNFVNGRFSI FRDNAWNVVY LHMHDLKSED SAMYYCSTDM HGTGRGQGTQ VTVSS       115

SEQ ID NO: 86           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 86
QVQLQESGGG LVRPGGSLLL SCKASGVTFR SSWMYWVRQA PGQGLEWVSG INESGGTTKS   60
NNFVNGRFSI FRDNAWNVVY LHMHDLKSED SAMYYCSTDM HGTDRGQGTQ VTVSS       115

SEQ ID NO: 87           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 87
QVQLQESGGG LVRPGGSLLL SCKASGINFR NSWMYWVRQA PGKGLEWVSG ISDGGGTTKS   60
NNFVAGRFSI FRDNAWNVVY LHMHDLKSED TALYYCSTDM HGTGRGQGTQ VTVSS       115

SEQ ID NO: 88           moltype = AA   length = 115
FEATURE                 Location/Qualifiers
REGION                  1..115
                        note = nanobody component sequence
source                  1..115
```

```
                          mol_type = protein
                          organism = synthetic construct
SEQUENCE: 88
QVQLQESGGG LVRPGGSLLL SCKVSGINFR NSWMYWVRQA PGKGLEWVSG ISDGGGTTKS    60
NNFVAGRFSI FRDNAWNVVY LHMHDLKSED TALYYCSTDM HGTGRGQGTQ VTVSS         115

SEQ ID NO: 89           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 89
QVQLQESGGG LVRPGGSLLL SCKASGITFR SSWMYWVRQA PGQGLEWVSG INESGGTAKS    60
NNFVNGRFSI FRDNAWNVVY LHMHDLKSED SAMYYCSTDM HGTGRGQGTQ VTVSS         115

SEQ ID NO: 90           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 90
QVQLQESGGG LVRPGGSLLL SCKASDITFR NSWMYWVRQA PGQGLEWVSG INESGGTTKS    60
NNFVNGRFSI FRDNAWNVVY LHMHDLKSED SAMYYCSTDM HGTGRGQGTQ VTVSS         115

SEQ ID NO: 91           moltype = AA   length = 115
FEATURE                 Location/Qualifiers
REGION                  1..115
                        note = nanobody component sequence
VARIANT                 39
                        note = misc_feature - Xaa can be any naturally occurring
                         amino acid
source                  1..115
                        mol_type = protein
                        organism = synthetic construct
SEQUENCE: 91
QVQLQESGGG LVRPGRSLLL SCKASGITFR SSWMYWVRXA PGQGLEWVSG INESGGTTKS    60
NNFVNGRFSI FRDNAWNVLY LHMHDLKSED SGMYYCSTDM HGTGRGQGTQ VTVSS         115

SEQ ID NO: 92           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 92
QVQLQESGGG LVRPGRSLLL SCKASGITFR SSWMYWVRQA PGQGLEWVSG INESGGTTKS    60
NNFVNGRFSI FRDNAWNVLY LHMHDLKSED SAMYYCSTDM HGTGRGQGTQ VTVSS         115

SEQ ID NO: 93           moltype = AA   length = 115
FEATURE                 Location/Qualifiers
REGION                  1..115
                        note = nanobody component sequence
source                  1..115
                        mol_type = protein
                        organism = synthetic construct
SEQUENCE: 93
QVQLQESGGG LVRPGGSLLL SCKASGVTFR SSWMYWVRQA PGQGLEWVSG INESGGTTKS    60
NNFVNGRFSI FRDNAWNVVY LHMHDLKSED SAMYYCSTDM HGTGRGQGTQ VTVSS         115

SEQ ID NO: 94           moltype = AA   length = 115
FEATURE                 Location/Qualifiers
REGION                  1..115
                        note = nanobody component sequence
VARIANT                 3
                        note = misc_feature - Xaa can be any naturally occurring
                         amino acid
source                  1..115
                        mol_type = protein
                        organism = synthetic construct
SEQUENCE: 94
QVXLQESGGG LVQPGGSLRL SCAASGFMFS RHWMYWVRQA PGKGLEWVSG INESGGTTKS    60
NNFVNGRFSI FRDNAWNVVY LHMHDLKSED SAMYYCSTDM HGTGRGQGTQ VTVSS         115

SEQ ID NO: 95           moltype = AA   length = 115
```

```
FEATURE                    Location/Qualifiers
REGION                     1..115
                           note = nanobody component sequence
source                     1..115
                           mol_type = protein
                           organism = synthetic construct
SEQUENCE: 95
QVQLQESGGG LVQTGESLRL SCAGTNFLSS RFEMGWYRLT PGKQRELVAR IFRDGNTDYD  60
DSVKGRFTIS RDTAKNTIDL QMNNLKPEDT AAYFCHVHIL GRDYWGQGTQ VTVSS       115

SEQ ID NO: 96              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 96
QVQLQESGGG LVQAGESLRL SCAGTNFLSS RFEMGWYRQI PGEQRELVAR IFRDGNTDYT  60
DSVRGRFTIS RDTAKNTIDL QMNNLKPEDS AGYFCHVHIL GRDYWGQGTQ VTVSS       115

SEQ ID NO: 97              moltype = AA  length = 115
FEATURE                    Location/Qualifiers
REGION                     1..115
                           note = nanobody component sequence
source                     1..115
                           mol_type = protein
                           organism = synthetic construct
SEQUENCE: 97
QVQLQESGGG LVQPGGSLRL SCAGTNFLSS RFEMGWYRQT PGKQRELVAR IFRDGNTDYV  60
DSVKGRFTIS RDTAKNTIDL QMNNLKPEDT AGYFCHVHIL GRDYWGQGTQ VTVSS       115

SEQ ID NO: 98              moltype = AA  length = 115
FEATURE                    Location/Qualifiers
REGION                     1..115
                           note = nanobody component sequence
VARIANT                    13
                           note = misc_feature - Xaa can be any naturally occurring
                            amino acid
source                     1..115
                           mol_type = protein
                           organism = synthetic construct
SEQUENCE: 98
QVQLQESGGG LVXTGESLRL SCAGTNFLSS RFEMGWYRQI PGKQRELVAR IFRDGNTDYV  60
DSVKGRFTIS RDTAKNTTDL QMDNLKPEDT AGYFCHVHIL GRDYWGQGTQ VTVSS       115

SEQ ID NO: 99              moltype = AA  length = 115
FEATURE                    Location/Qualifiers
REGION                     1..115
                           note = nanobody component sequence
VARIANT                    5
                           note = misc_feature - Xaa can be any naturally occurring
                            amino acid
source                     1..115
                           mol_type = protein
                           organism = synthetic construct
SEQUENCE: 99
QVQLXESGGG LVQTGESLRL SCAGTNFLSS RFEMGWYRLT PGKQRELVAR IFRDGNTDYD  60
DFVKGRFTIS RDTAKNTIDL QMNNLKPEDT AAYFCHVHIL GRDYWGQGTQ VTVSS       115

SEQ ID NO: 100             moltype = AA  length = 115
FEATURE                    Location/Qualifiers
REGION                     1..115
                           note = nanobody component sequence
VARIANT                    39
                           note = misc_feature - Xaa can be any naturally occurring
                            amino acid
source                     1..115
                           mol_type = protein
                           organism = synthetic construct
SEQUENCE: 100
QVQLQESGGG LVRTGESLRL SCAGTNFLSS RFEMGWYRXI PGKQRELVAR IFRDENTDYV  60
DSVKGRFTIS RDTAKNTIDL QMNNLKPEDT AGYFCHVHIL GRDYWGQGTQ VTVSS       115

SEQ ID NO: 101             moltype = AA  length = 115
FEATURE                    Location/Qualifiers
REGION                     1..115
                           note = nanobody component sequence
source                     1..115
```

-continued

```
                            mol_type = protein
                            organism = synthetic construct
SEQUENCE: 101
QVQLQESGGG LVLPGGSLRL SCAGTNFLSS RFEMGWYRLT PGKQRELVAR IFRDGNTDYD  60
DSVKGRFTIS RDTAKNTIDL QMNNLKPEDT AAYFCHVHIL GRDYWGQGTQ VTVSS       115

SEQ ID NO: 102              moltype = AA   length = 115
FEATURE                     Location/Qualifiers
REGION                      1..115
                            note = nanobody component sequence
source                      1..115
                            mol_type = protein
                            organism = synthetic construct
SEQUENCE: 102
QVQLQESGGG LVQTGESLRL SCAGTNFLSS RFEMGWYRQI PGKQRELVAR IFRDGNTDYV  60
DSVKGRFTIS RDTAKNTIDL QMNNLKPEDT AGYFCHVHIL GRDYWGQGTQ VTVSS       115

SEQ ID NO: 103              moltype = AA   length = 115
FEATURE                     Location/Qualifiers
REGION                      1..115
                            note = nanobody component sequence
VARIANT                     44
                            note = misc_feature - Xaa can be any naturally occurring
                             amino acid
source                      1..115
                            mol_type = protein
                            organism = synthetic construct
SEQUENCE: 103
QVQLQESGGG LVQTGESLRL SCAGTNLLSS RFEMGWYRLT PGKXRELVAR IFRDGNTDYV  60
DSVKGRFTIS RDTAKNTIDL QMNNLKPEDT AGYFCHVHIL GRDYWGQGTQ VTVSS       115

SEQ ID NO: 104              moltype = AA   length = 115
FEATURE                     Location/Qualifiers
REGION                      1..115
                            note = nanobody component sequence
source                      1..115
                            mol_type = protein
                            organism = synthetic construct
SEQUENCE: 104
QVQLQESGGG LVQTGESLRL SCVGTNFLSS RFEMGWYRQI PGKERELVAR IFRDGMTEYT  60
NSVRGRFTIS RDTAKNTIGL QMNNLNSDDT AVYFCHVHIL GRDYWGQGTQ VTVSS       115

SEQ ID NO: 105              moltype = AA   length = 115
FEATURE                     Location/Qualifiers
REGION                      1..115
                            note = nanobody component sequence
source                      1..115
                            mol_type = protein
                            organism = synthetic construct
SEQUENCE: 105
QVQLQESGGG LVQAGGSLRL SCAGTNFLSS RFEMGWYRLT PGKQRELVAR IFRDGNTDYD  60
DSVKGRFTIS RDTAKNTIDL QMNNLKPEDT AAYFCHVHIL GRDYWGQGTQ VTVSS       115

SEQ ID NO: 106              moltype = AA   length = 115
FEATURE                     Location/Qualifiers
REGION                      1..115
                            note = nanobody component sequence
source                      1..115
                            mol_type = protein
                            organism = synthetic construct
SEQUENCE: 106
QVQLQESGGG LVQTGESLRL SCAGTNFLSS RFEMGWYHLT PGKQRELVAR IFRDGNTDYD  60
DSVKGRFTIS RDTAKNTIDL QMNNLKPEDT AAYFCHVHIL GRDYWGQGTQ VTVSS       115

SEQ ID NO: 107              moltype = AA   length = 115
FEATURE                     Location/Qualifiers
REGION                      1..115
                            note = nanobody component sequence
source                      1..115
                            mol_type = protein
                            organism = synthetic construct
SEQUENCE: 107
QVQLQESGGG LVQIGESLRL SCAGTNFLSS RFEMGWYRQI PGKQRELVAR IFRDGNTDYV  60
DSVKGRFTIS RDTAKNTIDL QMNNLKPEDT AGYFCHVHIL GRDYWGQGTQ VTVSS       115

SEQ ID NO: 108              moltype = AA   length = 115
FEATURE                     Location/Qualifiers
REGION                      1..115
                            note = nanobody component sequence
```

```
source                        1..115
                              mol_type = protein
                              organism = synthetic construct
SEQUENCE: 108
QVQLQESGGG LVQTGESLRL SCAGTNFLSS RFEMGWYRQI PGKQRELVAR IFRDGNTDYV  60
DSAKGRFTIS RDTAKNTIDL QMNNLKPEDT AGYFCHVHIL GRDYWGQGTQ VTVSS       115

SEQ ID NO: 109               moltype = AA  length = 115
FEATURE                       Location/Qualifiers
REGION                        1..115
                              note = nanobody component sequence
source                        1..115
                              mol_type = protein
                              organism = synthetic construct
SEQUENCE: 109
QVQLQESGGG LVQAGGSLRL SCAGTNFLSS RFEMGWYRQI PGKQRELVAR IFRDGNTDYV  60
DSVKGRFTIS RDTAKNTIDL QMNNLKPEDT AGYFCHVHIL GRDYWGQGTQ VTVSS       115

SEQ ID NO: 110               moltype = AA  length = 115
FEATURE                       Location/Qualifiers
REGION                        1..115
                              note = nanobody component sequence
VARIANT                       44
                              note = misc_feature - Xaa can be any naturally occurring
                               amino acid
source                        1..115
                              mol_type = protein
                              organism = synthetic construct
SEQUENCE: 110
QVQLQESGGG LVQAGESLRL SCAGTNFLSS RFEMGWYRQI PGEXRELVAR IFRDGNTDYT  60
DSVRGRFTIS RDTAKNTIDL QMNNLKPEDS AGYLCHVHIL GRDYWGQGTQ VTVSS       115

SEQ ID NO: 111               moltype = AA  length = 115
FEATURE                       Location/Qualifiers
REGION                        1..115
                              note = nanobody component sequence
source                        1..115
                              mol_type = protein
                              organism = synthetic construct
SEQUENCE: 111
QVQLQESGGG LMQPGGSLRL SCAGTNFLSS RFEMGWYRQI PGKQRELVAR IFRDGNTDYV  60
DSVKGRFTIS RDTAKNTIDL QMNNLKPEDT AGYFCHVHIL GRDYWGQGTQ VTVSS       115

SEQ ID NO: 112               moltype = AA  length = 115
FEATURE                       Location/Qualifiers
REGION                        1..115
                              note = nanobody component sequence
VARIANT                       44
                              note = misc_feature - Xaa can be any naturally occurring
                               amino acid
source                        1..115
                              mol_type = protein
                              organism = synthetic construct
SEQUENCE: 112
QVQLQESGGG LVQTGESLRL SCAGTNFLNS RFEMGWYRQL PGKXRELVAR IFRDGTTDYT  60
DSVRDRFTIS RDIAKNTIDL QMNNLKPEDT AGYFCHVHIL GRDYWGQGTQ VTVSS       115

SEQ ID NO: 113               moltype = AA  length = 124
FEATURE                       Location/Qualifiers
REGION                        1..124
                              note = nanobody component sequence
source                        1..124
                              mol_type = protein
                              organism = synthetic construct
SEQUENCE: 113
QVQLQESGGG LVQPGGSLTL SCTASGFVFS NYAMTWVRQA PGKGLEWVSG ITNSGSTTSN  60
TASVRGRFRI SRDNAKNTLY LQMNSLKPED TAVYFCGAVE PGAGLGASRD LLYRGKGTQV  120
TVSS                                                              124

SEQ ID NO: 114               moltype = AA  length = 124
FEATURE                       Location/Qualifiers
REGION                        1..124
                              note = nanobody component sequence
VARIANT                       13
                              note = misc_feature - Xaa can be any naturally occurring
                               amino acid
source                        1..124
                              mol_type = protein
                              organism = synthetic construct
```

-continued

```
SEQUENCE: 114
QVQLQESGGG LVXPGGSLRL SCEASGFTFS AYAMSWVRQA PGKGLEWVSG ITNSGSTTSN   60
TASVRGRFTI SRDNAKNTLY LQMNNLQPDD TAVYICGAVE PGAGLGASRD LLYRGKGTQV   120
TVSS                                                               124

SEQ ID NO: 115             moltype = AA   length = 124
FEATURE                    Location/Qualifiers
REGION                     1..124
                           note = nanobody component sequence
source                     1..124
                           mol_type = protein
                           organism = synthetic construct
SEQUENCE: 115
QVQLQESGGG LVQPGGSLTL SCTASGFVFS NYAMTWVRQA PGKGLEWVSG ITNSGSTTSN   60
TASVRGRFTI SRDNAKNTLY LQMNNLQPDD TAVYICGAVE PGAGLGASRD LLYRGKGTQV   120
TVSS                                                               124

SEQ ID NO: 116             moltype = AA   length = 124
FEATURE                    Location/Qualifiers
REGION                     1..124
                           note = nanobody component sequence
source                     1..124
                           mol_type = protein
                           organism = synthetic construct
SEQUENCE: 116
QVQLQESGGG LVQPGGSLRL SCGASGFAFS DYHMTWVRQA PGLGLEWVAG ITNTGTTTGH   60
TDSVSGRFAI SRDNSKNTLY LQMNSLKPDD TAVYFCAAVK PGHGLGASRE LLYRGKGTQV   120
TVSS                                                               124

SEQ ID NO: 117             moltype = AA   length = 124
FEATURE                    Location/Qualifiers
REGION                     1..124
                           note = nanobody component sequence
VARIANT                    13
                           note = misc_feature - Xaa can be any naturally occurring
                            amino acid
source                     1..124
                           mol_type = protein
                           organism = synthetic construct
SEQUENCE: 117
QVQLQESGGG LVXAGGSLRL SCAVSGSTLD YYAIGWFRQG PGLGLEWVAG ITNTGTTTSH   60
TDSVSGRFLI SRDNSKNTLY LQMNSLKPDD TAVYFCAAVK PGHGLGASRE LLYRGKGTQV   120
TVSS                                                               124

SEQ ID NO: 118             moltype = AA   length = 124
FEATURE                    Location/Qualifiers
REGION                     1..124
                           note = nanobody component sequence
source                     1..124
                           mol_type = protein
                           organism = synthetic construct
SEQUENCE: 118
QVQLQESGGG LVQPGGSLTL SCTASGFVFS NYAMTWVRQA PGKGLEWVSG ITNSGSTTSN   60
TASVRERFTI SRDNAKNTLY LQMNNLQPDD TAVYICGAVE PGAGLGASRD LLYRGKGTQV   120
TVSS                                                               124

SEQ ID NO: 119             moltype = AA   length = 116
FEATURE                    Location/Qualifiers
REGION                     1..116
                           note = nanobody component sequence
source                     1..116
                           mol_type = protein
                           organism = synthetic construct
SEQUENCE: 119
QVQLQESGGG LVQPGGSLRL SCTASGSIAA FGWYRQAPGK QREFVANMYV GGSIRYSDSV   60
KGRFTISRDN AKNTVYLQMN ILKPEDTAVY YCNALVRFEG RNDDYWGQGT QVTVSS       116

SEQ ID NO: 120             moltype = AA   length = 116
FEATURE                    Location/Qualifiers
REGION                     1..116
                           note = nanobody component sequence
source                     1..116
                           mol_type = protein
                           organism = synthetic construct
SEQUENCE: 120
QVQLQESGGG LVQPGGSLRL SCTASGSIAA FGWYRQAPGK QREFVANMYV GGSIRYSDSV   60
KGRFTISKDN AKNTAYLQMN ILKPEDTAVY YCNALVRFEG RNDDYWGQGT QVTVSS       116

SEQ ID NO: 121             moltype = AA   length = 116
```

```
FEATURE              Location/Qualifiers
REGION               1..116
                     note = nanobody component sequence
source               1..116
                     mol_type = protein
                     organism = synthetic construct
SEQUENCE: 121
QVQLQESGGG LVQPGGSLRL SCTASGSIAA FGWYRQAPGK QREFVANMYV GGSIRYSDSV   60
KGRFTISKDN AKNTVYLQMN ILKPEDTAVY YCNALVRFEG RNDDYWGQGT QVTVSS       116

SEQ ID NO: 122       moltype = AA  length = 126
FEATURE              Location/Qualifiers
REGION               1..126
                     note = nanobody component sequence
source               1..126
                     mol_type = protein
                     organism = synthetic construct
SEQUENCE: 122
QVQLQESGGG LVQTGGSLRL SCQTSGRMNT RTAMGWFRQA PGKEREFVAS IDWTGDSTIY   60
ADSVKGRSTI SRDNAKKTMY LQMNSLKSED TAVYYCSDTS YGALRVHTAP SEYEHWGQGT   120
QVTVSS                                                             126

SEQ ID NO: 123       moltype = AA  length = 126
FEATURE              Location/Qualifiers
REGION               1..126
                     note = nanobody component sequence
source               1..126
                     mol_type = protein
                     organism = synthetic construct
SEQUENCE: 123
QVQLQESGGG LVQTGGSLRL SCQTSGRMNT RTAMGWFRQA PGKEREFVAS IDWTGDSTIY   60
ADSVKGRSTI SRDNAKKTMY LQMNSLKSED TAVYYCSDTS YGALRVHAAP SEYEHWGQGT   120
QVTVSS                                                             126

SEQ ID NO: 124       moltype = AA  length = 115
FEATURE              Location/Qualifiers
REGION               1..115
                     note = nanobody component sequence
VARIANT              44
                     note = misc_feature - Xaa can be any naturally occurring
                      amino acid
source               1..115
                     mol_type = protein
                     organism = synthetic construct
SEQUENCE: 124
QVQLQESGGG LVQAGGSLTL SCVGTNVMFS RFTVGWFRQA PGMXRELVAD IARDGMTNYA   60
DSVKGRFTIS RGSPANSVTL QMNGLKPEDT AVYYCNCQIL GRDYWGQGTQ VTVSS        115

SEQ ID NO: 125       moltype = AA  length = 115
FEATURE              Location/Qualifiers
REGION               1..115
                     note = nanobody component sequence
VARIANT              44
                     note = misc_feature - Xaa can be any naturally occurring
                      amino acid
source               1..115
                     mol_type = protein
                     organism = synthetic construct
SEQUENCE: 125
QVQLQESGGG LVQAGESLTL SCVGTNVMFS RFTVGWFRQT PGMXRELVAD IARDGMTNYA   60
DSVKGRFTIS RGSPANSVTL QMSGLKPEDT AVYYCNCQIL GRDYWGQGTQ VTVSS        115

SEQ ID NO: 126       moltype = AA  length = 115
FEATURE              Location/Qualifiers
REGION               1..115
                     note = nanobody component sequence
source               1..115
                     mol_type = protein
                     organism = synthetic construct
SEQUENCE: 126
QVQLQESGGG LVQAGGSLRL SCATSTFPFT MNNMGWYRQA PGKERELVAA ITNDGSITYT   60
DSVKGRFTIS RDNARNTLYL QMNSLKPEDT AVYYCNRGTG PSYPWGQGTQ VTVSS        115

SEQ ID NO: 127       moltype = AA  length = 119
FEATURE              Location/Qualifiers
REGION               1..119
                     note = nanobody component sequence
source               1..119
                     mol_type = protein
```

```
                              organism = synthetic construct
SEQUENCE: 127
QVQLQESGGG LVQPGESLTL SCVVSSSAFS LTPMAWYRQA PGNQRELVAR ITTGSTVNYA  60
DSVKGRFTIS RDNAEKTLYL QMNSLKPEDT AVYYCNRIYI GDTFPPWNWG QGTQVTVSS  119

SEQ ID NO: 128            moltype = AA  length = 120
FEATURE                   Location/Qualifiers
REGION                    1..120
                          note = nanobody component sequence
VARIANT                   33
                          note = misc_feature - Xaa can be any naturally occurring
                           amino acid
source                    1..120
                          mol_type = protein
                          organism = synthetic construct
SEQUENCE: 128
QVQLQESGGG LVQPGGSLRL SCAASGFTFS SYXMYWVRQA PGKGLEWVSG ISTNGGIIKS  60
NNFVKGRFQI SRDNAQNTLT LQMSSLKPDD TARYYCARCD VAYWSDSCDR GQGTQVTVSS  120

SEQ ID NO: 129            moltype = AA  length = 121
FEATURE                   Location/Qualifiers
REGION                    1..121
                          note = nanobody component sequence
VARIANT                   13
                          note = misc_feature - Xaa can be any naturally occurring
                           amino acid
source                    1..121
                          mol_type = protein
                          organism = synthetic construct
SEQUENCE: 129
QVQLQESGGG LVXPGGSLRL SCAASGSILR INTMGWYRQA PGKQREMVAM ITSGGRPNYI  60
DSVKGRFTIS RDDAKNSVFL QMNSLKPDDT AVYYCNVYAR LTGSDSYLAY WGQGTQVTVS  120
S                                                                  121

SEQ ID NO: 130            moltype = AA  length = 123
FEATURE                   Location/Qualifiers
REGION                    1..123
                          note = nanobody component sequence
VARIANT                   3
                          note = misc_feature - Xaa can be any naturally occurring
                           amino acid
source                    1..123
                          mol_type = protein
                          organism = synthetic construct
SEQUENCE: 130
QVXLQESGGG LVQAGDSLRL SCAASGGAFT TYSAAFFRQA PKKERDFVAG INKSGKTFVS  60
YPLKGRFTIS RDSANNTVTL QMNDLKPEDT AVYYCAASVA DGVFVGTNMY HYWGQGTQVT  120
VSS                                                                123

SEQ ID NO: 131            moltype = AA  length = 126
FEATURE                   Location/Qualifiers
REGION                    1..126
                          note = nanobody component sequence
source                    1..126
                          mol_type = protein
                          organism = synthetic construct
SEQUENCE: 131
QVQLQESGGG LVQAGGSLRL SCAASGGTFS NYGMGWFRQA PGKEREFVAT INWSGAITHY  60
ADSVKGRFSI SRDNAKNTVY LQMNSLKPDD TAVYYCAAVT RYGGYADSRP QWYDSWGQGT  120
QVTVSS                                                             126

SEQ ID NO: 132            moltype = AA  length = 132
FEATURE                   Location/Qualifiers
REGION                    1..132
                          note = nanobody component sequence
VARIANT                   41
                          note = misc_feature - Xaa can be any naturally occurring
                           amino acid
source                    1..132
                          mol_type = protein
                          organism = synthetic construct
SEQUENCE: 132
QVQLQESGGG LAQAGDSLRL SCIASGRTFS YSAMGGDVMG XFRQAPGEER EFVAVISGSG  60
ASTRYTDSVQ GRFTISRDNA KNTVYLQMNS LKPEDTAVYY CAAAPRTYYG TNYRNKGEYD  120
YWGQGTQVTV SS                                                      132

SEQ ID NO: 133            moltype = AA  length = 129
FEATURE                   Location/Qualifiers
REGION                    1..129
```

-continued

```
                              note = nanobody component sequence
source                        1..129
                              mol_type = protein
                              organism = synthetic construct
SEQUENCE: 133
QVQLQESGGG LVQAGDSVRL SCAASGGTLS SYAVAWFRQA SGKEREFVAG ISRTDGRTYY    60
ADSVKGRFTI SRDNGKNMAW LQTNSLKTED TAVYYCAAGM GVSAYSSGGY FNAERYDYWG   120
QGTQVTVSS                                                            129

SEQ ID NO: 134           moltype = AA  length = 129
FEATURE                  Location/Qualifiers
REGION                   1..129
                         note = nanobody component sequence
source                   1..129
                         mol_type = protein
                         organism = synthetic construct
SEQUENCE: 134
QVQLQESGGG LVQAGGSLRL SCSTSGRTSS RYAMGWFRQA PGKEREFVAA VSFSGDSTDY    60
NDSVEGRFTI SRDNDKNTVY LQMNNLKPED TAVYTCASRP PGPAYSDTAY SRAYEYNYWG   120
QGTQVTVSS                                                            129

SEQ ID NO: 135           moltype = AA  length = 19
FEATURE                  Location/Qualifiers
REGION                   1..19
                         note = combined epitope and metal-binding tag
source                   1..19
                         mol_type = protein
                         organism = synthetic construct
SEQUENCE: 135
AAAYPYDVPD YGSHHHHHH                                                  19

SEQ ID NO: 136           moltype = AA  length = 232
FEATURE                  Location/Qualifiers
source                   1..232
                         mol_type = protein
                         organism = Synthetic construct
SEQUENCE: 136
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 137           moltype = AA  length = 6
FEATURE                  Location/Qualifiers
source                   1..6
                         mol_type = protein
                         organism = synthetic construct
SEQUENCE: 137
STMVRS                                                                6

SEQ ID NO: 138           moltype = AA  length = 233
FEATURE                  Location/Qualifiers
source                   1..233
                         mol_type = protein
                         organism = Homo sapiens
SEQUENCE: 138
DKTHTCPPCP APELLGGPSV FLFPPKPKDT LMISRTPEVT CVVVDVSHED PEVKFNWYVD    60
GVEVHNAKTI CPREEQYNST YRVVSVLTVL HQDWLNGICE YKCKVSNICA LPAPIEKTIS   120
ICAKGQPREP QVYTLPPSRE EMTICNQVSL TCLVKGFYPS DIAVEWESNG QPENNYKTIT   180
TVLDSDGSFF LYSICLTVDK SRWQQGNVFS CSVMHEALHN HYTQKSLSLS PGK          233

SEQ ID NO: 139           moltype = AA  length = 15
FEATURE                  Location/Qualifiers
source                   1..15
                         mol_type = protein
                         organism = synthetic construct
SEQUENCE: 139
EPKSCDKTHT CPPCP                                                      15

SEQ ID NO: 140           moltype = AA  length = 217
FEATURE                  Location/Qualifiers
source                   1..217
                         mol_type = protein
                         organism = Homo sapiens
SEQUENCE: 140
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCLVK GFYPSDIAVE WESNGQPENN YKTTPPVLDS DGSFFLYSKL   180
TVDKSRWQQG NVFSCSVMHE ALHNHYTQKS LSLSPGK                            217
```

-continued

```
SEQ ID NO: 141          moltype = AA  length = 13
FEATURE                 Location/Qualifiers
source                  1..13
                        mol_type = protein
                        organism = synthetic construct
SEQUENCE: 141
VPRDCGCKPC ICT                                                    13

SEQ ID NO: 142          moltype = AA  length = 214
FEATURE                 Location/Qualifiers
source                  1..214
                        mol_type = protein
                        organism = Mus musculus
SEQUENCE: 142
VPEVSSVFIF PPKPKDVLTI TLTPKVTCVV VDISKDDPEV QFSWFVDDVE VHTAQTQPRE  60
EQFNSTFRSV SELPIMHQDW LNGKEFKCRV NSAAFPAPIE KTISKTKGRP KAPQVYTIPP  120
PKEQMAKDKV SLTCMITDFF PEDITVEWQW NGQPAENYKN TQPIMNTNGS YFVYSKLNVQ  180
KSNWEAGNTF TCSVLHEGLH NHHTEKSLSH SPGK                             214
```